US010893985B2

(12) United States Patent
Ishikawa et al.

(10) Patent No.: US 10,893,985 B2
(45) Date of Patent: Jan. 19, 2021

(54) ELASTIC STRUCTURE FOR ABSORBENT ARTICLE AND METHOD FOR MANUFACTURING ELASTIC STRUCTURE FOR ABSORBENT ARTICLE

(71) Applicant: Daio Paper Corporation, Ehime (JP)

(72) Inventors: Yasuko Ishikawa, Ehime (JP); Keisuke Ebiduka, Ehime (JP); Shunji Seno, Ehime (JP)

(73) Assignee: DAIO PAPER CORPORATION, Ehime (JP)

( * ) Notice: Subject to any disclaimer, the term of this patent is extended or adjusted under 35 U.S.C. 154(b) by 797 days.

(21) Appl. No.: 14/781,257

(22) PCT Filed: Mar. 20, 2014

(86) PCT No.: PCT/JP2014/057750
§ 371 (c)(1),
(2) Date: Nov. 23, 2015

(87) PCT Pub. No.: WO2014/156949
PCT Pub. Date: Oct. 2, 2014

(65) Prior Publication Data
US 2016/0067115 A1    Mar. 10, 2016

(30) Foreign Application Priority Data

Mar. 29, 2013  (JP) .................. 2013-075214
Mar. 29, 2013  (JP) .................. 2013-075216
(Continued)

(51) Int. Cl.
*A61F 13/494*    (2006.01)
*A61F 13/49*     (2006.01)
(Continued)

(52) U.S. Cl.
CPC ...... *A61F 13/494* (2013.01); *A61F 13/15593* (2013.01); *A61F 13/15699* (2013.01);
(Continued)

(58) Field of Classification Search
CPC .. B32B 3/085; B32B 3/10; B32B 3/22; B32B 3/16; B32B 5/022; B32B 5/24;
(Continued)

(56) References Cited

U.S. PATENT DOCUMENTS 5,576,090 A  * 11/1996  Suzuki ............. A61F 13/15593
                                                      156/164
6,291,039 B1   9/2001  Combe et al.
(Continued)

FOREIGN PATENT DOCUMENTS

JP   H03-213543   9/1991
JP   H13-213543   9/1991
(Continued)

OTHER PUBLICATIONS

English translation of JP 2010022588, epsacenet, tranlsated Feb. 8, 2018.*
(Continued)

*Primary Examiner* — Jennifer A Gillett
(74) *Attorney, Agent, or Firm* — Muncy, Geissler, Olds and Lowe, P.C.

(57) ABSTRACT

An object of the present invention is to provide an elastic structure that has straightly extended ridges with excellent appearance, air permeability, and fluffy feel. The object can be attained by an elastic structure in which a first sheet material (12S) and a second sheet material (12H) are joined together to form sheet joined sections (70) by an adhesive (71) applied intermittently in an extending direction and continuously in a direction intersecting with the extending direction, resilient and elastic members (15 and 16) are fixed
(Continued)

by the adhesive (71) to at least one of the first sheet material (12S) and the second sheet material (12H) at intersections with the sheet joined sections (70), and when the first sheet material (12S) and the second sheet material (12H) are contracted with contraction of the resilient and elastic members (15 and 16), portions of the first sheet material (12S) and the second sheet material (12H) positioned between the sheet joined sections (70) are swelled in mutually opposite directions to form ridges (80), and the sheet joined sections (70) have a width (70*w*) of 0.5 to 4 mm in the extending direction and spacing (70*d*) between the adjacent sheet joined sections (70) is 4 to 8 mm.

3 Claims, 16 Drawing Sheets

(30) Foreign Application Priority Data

Mar. 29, 2013 (JP) .................................. 2013-075217
Mar. 10, 2014 (JP) .................................. 2014-046524

(51) Int. Cl.
*A61F 13/15* (2006.01)
*A61F 13/496* (2006.01)

(52) U.S. Cl.
CPC ........ *A61F 13/4902* (2013.01); *A61F 13/496* (2013.01); *A61F 13/49011* (2013.01); *A61F 13/49014* (2013.01); *A61F 2013/4948* (2013.01)

(58) Field of Classification Search
CPC ....... B32B 2307/51; A61F 2013/49025; A61F 2013/49011
USPC ........ 442/328, 329, 381, 414; 428/196, 201, 428/214, 219; 604/385.27, 385.24
See application file for complete search history.

(56) References Cited

U.S. PATENT DOCUMENTS

| | | | |
|---|---|---|---|
| 2005/0038401 A1* | 2/2005 | Suzuki | A61F 13/495 604/385.01 |
| 2006/0270302 A1 | 11/2006 | Ando | |
| 2012/0310193 A1 | 12/2012 | Ostertag | |

FOREIGN PATENT DOCUMENTS

| | | |
|---|---|---|
| JP | 22926/1992 | 2/1992 |
| JP | 71922/1992 | 6/1992 |
| JP | 3212615 B2 | 9/2001 |
| JP | 2004-115667 | 4/2004 |
| JP | 2007-169531 | 7/2007 |
| JP | 2008131968 A | 6/2008 |
| JP | 2008132023 A | 6/2008 |
| JP | 2008132024 A | 6/2008 |
| JP | 2008154998 | 7/2008 |
| JP | 2008154998 A | 7/2008 |
| JP | 2008173286 A | 7/2008 |
| JP | 2008229246 A | 10/2008 |
| JP | 2008-295930 | 12/2008 |
| JP | 2009106667 | 5/2009 |
| JP | 2009-118986 | 6/2009 |
| JP | 2009-148447 | 7/2009 |
| JP | 2009-207698 | 9/2009 |
| JP | 2009-297096 | 12/2009 |
| JP | 2010-22588 | 2/2010 |
| JP | 2010-46324 | 3/2010 |
| JP | 2010200831 A | 9/2010 |
| JP | 2011177285 A | 9/2011 |
| JP | 2012024464 A | 2/2012 |
| JP | 2012200295 A | 10/2012 |
| JP | 2013-34850 | 2/2013 |
| JP | 2013027600 A | 2/2013 |

OTHER PUBLICATIONS

English translation of JP 2004115667, espacenet translated Mar. 5, 2018.*

* cited by examiner (a)

(b)

PRIOR ART (Sample No. 13)

(Sample No. 14)

ELASTIC STRUCTURE FOR ABSORBENT ARTICLE AND METHOD FOR MANUFACTURING ELASTIC STRUCTURE FOR ABSORBENT ARTICLE

TECHNICAL FIELD

The present invention relates to an elastic structure for absorbent article formed by fixing elongated resilient and elastic members in an elongated state between layered sheet materials, more specifically, an elastic structure for absorbent article that has straightly extended ridges with excellent appearance, air permeability, and fluffy feel (the property of recovering flexibly from the compressed state in a thickness direction), and a method for manufacturing the elastic structure for absorbent article.

BACKGROUND ART

For example, an underpants-type disposable diaper includes an outer body that has a front body part and a back body part, and an inner body that is fixed to the inner surface of the outer body and includes an absorber. The front body part and the back body part of the outer body are joined together at the both sides to form a waist opening and a pair of right and left leg openings.

In the underpants-type disposable diaper, in order to enhance a fit to the human body, elongated resilient and elastic members such as rubber threads are fixed in an elongated state at several sections of the outer body along a circumferential direction to form an elastic structure along the waist portion. In particular, diapers including waist-edge portion resilient and elastic members at the edge portion of the waist opening along the width direction and waist lower portion resilient and elastic members closer to the crotch portion than the waist-edge resilient and elastic members, are widely used due to their relatively good fit to the human body.

Meanwhile, a tape-type disposable diaper has a crotch portion, a ventral-side portion extended to the front side of the crotch portion, a back-side portion extended to the back side of the crotch portion, an absorber provided in an area including the crotch portion, fastening tapes protruding from the both sides of the back portion, and target tapes positioned on the outer surface of the ventral-side portion to which the fastening tapes are to be fastened. To put the diaper on the wearer's body, the fastening tapes are turned from the both sides of the waist toward the outer surface of the ventral-side portion and are fastened to the target tapes. The tape-type disposable diapers are used for infants and for recipients of care (adults) as well. In general, the tape-type disposable diapers are inferior in a fit around the waist to the underpants-type disposable diapers. To improve this, elongated resilient and elastic members such as rubber threads are fixed in an elongated state to the back-side portion and the fastening tapes along the width direction to form an elastic structure along the waist portion.

In addition, to improve these elastic structures, there has been proposed an elastic structure in which two sheet materials 12H and 12S are intermittently joined together in an extending direction and a direction orthogonal to the extending direction to form a large number of sheet joined sections 70 as illustrated in FIG. 14 (refer to Patent Documents 1 to 3. The elastic structure will be hereinafter also referred to as vertical intermittent joining mode). According to the related art, the vertical alignment of the sheet joined sections 70 constitutes vertically continuous grooves, and the sections between the grooves form large ridges 80 that swell to the same degree on the both front and back sides. The grooves improve air permeability and the ridges 80 produce excellent fluffy feel. In FIG. 14, reference sign 75 indicates welded portions of the sheet materials 12H and 12S. The sheet joined sections 70 may be formed by the use of an adhesive to produce the ridges 80 identical in shape to the foregoing ridges 80.

However, the related art has a problem that the ridges take the shape of fluffy feel clouds or waves with inferior appearance and air permeability.

Meanwhile, there has been known a technique by which two sheet materials are adhered to each other intermittently in the extending direction and continuously in the direction intersecting with the extending direction to form a large number of sheet joined sections (for example, refer to Patent Document 4. This form will be hereinafter also referred to as a vertical continuous joining mode).

However, this related art includes straightly extended ridges with excellent appearance and air permeability, but produces inferior fluffy feel (the property of recovering flexibly from the compressed state in a thickness direction).

CITATION LIST

Patent Documents

Patent Document 1: JP 2008-295930 A
Patent Document 2: JP 2009-297096 A
Patent Document 3: JP 2009-148447 A
Patent Document 4: JP 2010-22588 A

SUMMARY OF INVENTION

Technical Problem

Therefore, a main issue of the present invention is to provide an elastic structure that has straightly extended ridges with excellent appearance and air permeability and produces excellent fluffy feel, and a method for manufacturing an elastic structure for an absorbent article.

Solution to Problem

The inventor of the present invention has earnestly studied solutions to the foregoing issue and has achieved findings described below (the principles described herein and their differences have not been sought for in any of Patent Documents 1 to 4. In particular, Patent Document 4 has a description of the spacing between lines of the sheet joined sections but does not discuss the influence of changes in the sp acing).

Specifically, in the vertical intermittent joining mode in which a plurality of elongated resilient and elastic members 19 is arranged independently from the sheet materials 12H and 12S, not passing through the sheet joined sections 70 between the sheet materials 12H and 12S (but passing through the non-joined sections) as illustrated in FIG. 14 (the forms described in Patent Documents 1 and 2 are applied), the resilient and elastic members 19 are fixed to the sheets at the both end portions (not illustrated), not at the positions corresponding to the sheet joined sections 70 in the extending direction. Accordingly, even though the ridges 80 are gathered by contraction force of the resilient and elastic members 19, the ridges 80 are not formed between the sheet joined sections 70 adjacent to each other in the extending direction resulting from the direct action of contraction of the resilient and elastic members 19, but the contraction of the resilient and elastic members 19 acts on the fixed portions of both ends of the resilient and elastic members 19, the entire sheet materials between the fixed portions are gathered in the width direction, and the sections of the sheet materials other than the sheet joined sections 70 are indirectly swelled to form the ridges 80. As a result, even though the ridges 80 are positioned vertically in correspondence with the sheet joined sections 70, the spacing between the sheet joined sections 70 becomes wider in the extending direction to form the ridges 80 in a round, full-figured shape as illustrated in FIG. 14(b). In addition, the ridges 80 are further round and full-figured at the positions through which the resilient and elastic members 19 pass as illustrated in FIG. 14(c).

In the vertical intermittent joining mode, however, the spacing between the ridges 80 is narrow and less effective in improvement of air permeability. In addition, when the ridges 80 are formed by the indirect action of contraction force of the resilient and elastic members 19 and the sheet joined sections 70 are arranged intermittently in the vertical direction, the spacing between the sheet joined sections 70 is vertically changed in a cyclic manner to generate a difference between the swelled shape of the ridges 80 positioned corresponding to the sheet joined sections 70 in the vertical direction and the swelled shape of the ridges 80 positioned between the joined sections in the vertical direction as seen from the comparison between FIGS. 14(b) and 14(c). Accordingly, the ridges 80 take the shape of gathering clouds or waves with inferior appearance and air permeability. When the resilient and elastic members are arranged to pass through the sheet joined sections as described in Patent Document 3, the contraction force of the resilient and elastic members acts directly on the sheet joined sections. However, the sheet joined sections are arranged intermittently in the vertical direction to generate a difference between the swelled shapes of the ridges positioned corresponding to the sheet joined sections in the vertical direction and the swelled shape of the ridges positioned between the joined sections in the vertical direction. Accordingly, as in the foregoing case, the ridges take the shape of gathering clouds or waves with inferior appearance and air permeability.

Meanwhile, in the vertical continuous joining mode, the sheet joined sections are vertically continued, and the resilient and elastic members are fixed to the sheet at the positions corresponding to the sheet joined sections in the extending direction. Accordingly, the spacing between the sheet joined sections in the extending direction is uniform even when the resilient and elastic members are positioned corresponding to the sheet joined sections in the vertical direction or are arranged at the positions through which the resilient and elastic members pass. This produces the ridges extended in a straight line with excellent appearance and air permeability.

However, the resilient and elastic members are fixed to the sheet at the positions corresponding to the sheet joined sections in the extending direction, and the contraction of the resilient and elastic members acts directly on the sheet joined sections adjacent to each other in the extending direction. Accordingly, the sheet joined sections are directly gathered to form the ridges. As a result, the spacing between the sheet joined sections is very narrow to make the ridges thin and relatively tapered down toward their tips. The ridges are therefore likely to be fallen, and are thin and poor in fluffy feel.

That is, in the vertical continuous joining mode, the shape of the ridges and principles of formation of the ridges are completely different from those in the intermittent joining mode, and it has thus not been known whether the matter working in one mode also works in the other. The inventor of the present invention has further conducted studies based on the foregoing findings to achieve the present invention. Specifically, the present invention as a solution to the foregoing issue is as described below.

In accordance with an exemplary embodiment of the invention, an elastic structure for absorbent article, includes a first sheet material; a second sheet material opposed to one surface of the first sheet material; and a plurality of elongated resilient and elastic members that is provided between the first sheet material and the second sheet material along an extending direction with spacing therebetween, wherein the first sheet material and the second sheet material are joined together to form sheet joined sections by an adhesive applied intermittently in the extending direction and continuously in a direction intersecting with the extending direction, the resilient and elastic members are fixed by an adhesive to at least one of the first sheet material and the second sheet material at intersections with the sheet joined sections, when the first sheet material and the second sheet material are contracted with contraction of the resilient and elastic members, portions of the first sheet material and the second sheet material positioned between the sheet joined sections are swelled in mutually opposite directions to form ridges, and the sheet joined sections have a width of 0.5 to 4 mm in the extending direction and spacing between the adjacent sheet joined sections is 4 to 8 mm.

(Operation and Effect)

The present invention is characterized in that, in the vertical continuous joining mode, the spacing between the adjacent sheet joined sections and the width of the sheet joined sections in the extending direction are combined within a specific range to provide the ridges extended in a straight line with a compatibility between sufficient height and resistance to being fallen. In the present invention, the width of the sheet joined sections in the extending direction affects the spacing between the adjacent ridges. In the case where the ridges are thin as in the vertical continuous joining mode and the width of the sheet joined sections is larger than 4 mm, the spacing between the adjacent ridges is excessively large to make the individual ridges appear to be independent from each other. In addition, when the ridges are deformed to be flattened and spread or fallen by the contraction force in the thickness direction, the adjacent ridges support imperfectly each other and become weakened in resistance against deformation and recovery from deformation, thereby resulting in insufficient fluffy feel.

Further, when the width of the sheet joined sections in the extending direction is 0.5 to 4 mm but the spacing between the adjacent sheet joined sections is less than 4 mm or larger than 8 mm, some problems will arise as described below. The spacing between the adjacent joined sections affects the height and width of the ridges. With a spacing of about 2 mm, the ridges are insufficient in vertical continuity as in the case where the sheet materials are joined continuously in the extending direction (it is useless to provide the intermittent sheet joined sections in the extending direction). Meanwhile, with a spacing of 3 mm, the ridges are extended in a straight line in the direction orthogonal to the extending direction, but the adjacent ridges support insufficiently each other with a shortage of fluffy feel. When the spacing between the sheet joined sections is more than 8 mm, the ridges are randomly compressed and crushed at the time of packaging, which deteriorates the appearance of the product. In contrast, when the width of the sheet joined sections in the extending direction is set to 0.5 to 4 mm and the spacing between the sheet joined sections is set to 4 to 8 mm, the ridges produce sufficient fluffy feel and become less prone to be randomly compressed and crushed at the time of packaging.

In the vertical continuous joining mode, when the sheet joined sections are formed by welding, hard streaks are generated with inevitable reduction in flexibility. In the present invention, however, the sheet joined sections are formed by an adhesive without reduction in flexibility resulting from material welding, thereby providing further excellent flexibility.

In the present invention, the mode in which the adhesive is continuously applied to form the sheet joined sections includes the mode in which the adhesive is continuously applied to both the first sheet material and the second sheet material in the direction intersecting with the extending direction at the intersections between the sheet joined sections and the resilient and elastic members, and the mode in which the adhesive is continuously applied to one of the sheet materials but the adhesive is discontinuously applied to the other in the direction intersecting with the extending direction due to the intervention of the resilient and elastic members.

In the present invention, the mode in which the resilient and elastic members are fixed by an adhesive to the sheet materials at the intersections with the sheet joined sections includes the mode in which the resilient and elastic members and the sheet materials are adhered to each other by the adhesive for forming the sheet joined sections at the positions where the resilient and elastic members and the sheet joined section intersect each other, and the mode in which another adhesive for fixing the resilient and elastic members is separately applied.

In accordance with an exemplary embodiment of the invention, the first sheet material and the second sheet material are non-woven fabric in which the bending resistance is higher in the extending direction than in the direction orthogonal to the extending direction.
(Operation and Effect)

The first sheet material and the second sheet material are preferably non-woven fabric. However, if the bending resistance is low in the extending direction, the ridges become thin and sharp in shape, likely to be fallen, and poor in compression resilience in the thick direction. To solve these problems, the basis weight of the non-woven fabric may be increased. In this case, however, the sheet materials may become stiff (due to excessively high rigidity) and less soft to the touch in spite of their fluffy appearances. Meanwhile, when the first sheet material and the second sheet material are made from non-woven fabric in which the bending resistance is higher in the extending direction than in the direction orthogonal to the extending direction, the ridges are likely to be roundly swelled, increased in compression resilience in the thickness direction, less prone to be fallen, and improved in softness to the touch.

In accordance with an exemplary embodiment of the invention, the adhesive is a hot-melt adhesive with a melt viscosity of 10000 mpas or less at a temperature of 140° C., a melt viscosity of 5000 mpas or less at a temperature of 160° C., and a loop tack adhesive force of 2000 g/25 mm or more.
(Operation and Effect)

The adhesive for forming the sheet joined sections is preferably a hot-melt adhesive. However, if the width of the sheet joined sections in the extending direction is to be small, for example, 1 mm or less, the hot-melt adhesive needs to be applied with a smaller width and it is very difficult to apply the adhesive by spraying from a nozzle. In addition, even in the case of using a pattern coating method suited to narrow-width application (transfer of a hot-melt adhesive by a relief printing technique), it is considered that some types of hot-melt adhesive become stringy to cause degradation in accuracy of application width (that is, the width of the sheet joined sections) and reduction in stability of operation, taking into account the presently general production line speed in Japan. In contrast, by using the hot-melt adhesive with the melt viscosity and loop tack adhesive force as described above, it is possible to improve the accuracy of application width and the stability of operation without stringiness of the adhesive even at the presently general production line speed in Japan.

In accordance with an exemplary embodiment of the invention, at the intersections between the sheet joined sections and the resilient and elastic members, the adhesive is continuously applied to the resilient and elastic members at the first sheet material side in the direction intersecting with the extending direction, so that the resilient and elastic members are fixed by the adhesive to the first sheet material, and the adhesive is discontinuously applied to the resilient and elastic members at the second sheet material side in the direction intersecting with the extending direction.
(Operation and Effect)

As described above, the adhesive is intermittently applied to the second sheet material to suppress reduction in flexibility of the second sheet material, and also suppress reduction in flexibility of the first sheet material and the second sheet material as a whole. In addition, although the adhesive is continuously applied to only the resilient and elastic members at the first sheet material side at the intersections with the sheet joined sections, the first sheet material and the second sheet material are unified by the sheet joined sections at the both sides of the resilient and elastic members. Accordingly, the contraction force of the resilient and elastic members acts substantially equally on the first sheet material and the second sheet material to form uniform wrinkles in the first sheet material and the second sheet material.

In accordance with an exemplary embodiment of the invention, the second sheet material has a surface to be in contact with a wearer's skin, and the first sheet material is joined to a surface of the second sheet material opposite to the surface to be in contact with the wearer's skin.
(Operation and Effect)

In the case where either the first sheet material or the second sheet material is to be in contact with the wearer's skin, when the sheet material to be in contact with the skin has the continuously applied adhesive, the sheet material is lower in flexibility and provides a worse feel because the surface of the sheet material with lower flexibility is pressed against the skin by the resilient and elastic members. Accordingly, it is desired that the second sheet material has the surface with the discontinuously applied adhesive to be in contact with the skin as described above.

In accordance with an exemplary embodiment of the invention, an elastic structure for absorbent article, includes a first sheet material; a second sheet material opposed to one surface of the first sheet material; and a plurality of elongated resilient and elastic members that is provided between the first sheet material and the second sheet material along an extending direction with spacing therebetween, wherein the first sheet material and the second sheet material are joined together to form sheet joined sections by a welding process performed intermittently in the extending direction and continuously in a direction intersecting with the extending direction, the resilient and elastic members are fixed to at least one of the first sheet material and the second sheet material at intersections with the sheet joined sections, when the first sheet material and the second sheet material are contracted with contraction of the resilient and elastic members, portions of the first sheet material and the second sheet material positioned between the sheet joined sections are swelled in mutually opposite directions to form ridges, and the sheet joined sections have a width of 0.5 to 4 mm in the extending direction and spacing between the adjacent sheet joined sections is 4 to 8 mm.

(Operation and Effect)

In the invention according to claim 6, the same operation and effect as those in the invention according to claim 1 can be obtained.

When the sheet joined sections are formed by welding in the vertical continuous joining mode as in the invention according to claim 6, the welded portions become inevitably hardened. However, the influence of the hardening is limited when the dimensions of the sheet joined sections fall within the foregoing range. In addition, the welding process produces a secondary effect that the welded portions are higher in transparency and appear to be glossy in a striped pattern.

In the present invention, the mode in which the welding process for forming the sheet joined sections is continuously performed includes the mode in which, as far as the welding trace resides continuously on at least one of the first sheet material and the second sheet material, the first sheet material and the second sheet material and the resilient and elastic members are welded to each other and the first sheet material and the second sheet material are indirectly welded to each other to make the welding continuous, and the mode in which the welding is not continuous between the first sheet material and the second sheet material because the resilient and elastic members intervene at the intersections between the sheet joined sections and the resilient and elastic members.

In addition, the mode in which the resilient and elastic members are fixed to the sheet at the intersections with the sheet joined sections includes the mode in which the resilient and elastic members and the sheet are adhered to each other (or welded to each other, which is also applied to the subsequent description) at the intersections between the resilient and elastic members and the sheet joined sections, and the mode in which the resilient and elastic members and the sheet are not adhered to each other but the contraction force of the resilient and elastic members is transferred to the sheet at the intersections with the sheet joined sections because the spacing between the sheet joined sections in the direction intersecting with the extending direction is smaller than the thickness of the resilient and elastic members in the natural length state and the resilient and elastic members are sandwiched and fixed between the sheet joined sections. The latter mode is described in JP 2008-154998 A and JP 2009-106667 A, which is different from the modes described in Patent Documents 1 to 3 in that the designed positions of the elastic members at the side part pass through the sheet joined sections.

In accordance with an exemplary embodiment of the invention, the first sheet material and the second sheet material are non-woven fabric in which the bending resistance is higher in the extending direction than in the direction orthogonal to the extending direction.

(Operation and Effect)

The first sheet material and the second sheet material are preferably non-woven fabric. However, if the bending resistance is low in the extending direction, the ridges become thin and sharp in shape, likely to be fallen, and poor in compression resilience in the thick direction. To solve these problems, the basis weight of the non-woven fabric may be increased. In this case, however, the sheet materials may become stiff (due to excessively high rigidity) and less soft to the touch in spite of their fluffy appearances. Meanwhile, when the first sheet material and the second sheet material are made from non-woven fabric in which the bending resistance is higher in the extending direction than in the direction orthogonal to the extending direction, the ridges are likely to be roundly swelled, increased in compression resilience in the thickness direction, less prone to be fallen, and improved in softness to the touch.

In accordance with an exemplary embodiment of the invention, the spacing between the adjacent resilient and elastic members is 10 mm or less.

(Operation and Effect)

In the present invention, when the spacing (not central clearance) between the adjacent resilient and elastic members exceeds 10 mm, the thickness of the ridges changes in the direction intersecting with the extending direction to take the shape of gathering clouds or waves although it is less prominent than in the vertical intermittent joining mode. Accordingly, in the present invention, the spacing between the adjacent resilient and elastic members is preferably 10 mm or less.

In accordance with an exemplary embodiment of the invention, the first sheet material and the second sheet material are non-woven fabric with a thickness of 0.1 to 1 mm and a basis weight of 10 to 20 g/m².

(Operation and Effect)

The present invention is particularly suited to the first sheet material and the second sheet material as described above.

In accordance with an exemplary embodiment of the invention, an extension ratio of the resilient and elastic members is 200 to 350% in a state where the elastic structure is fully opened.

(Operation and Effect)

At the extension ratio as described above, the aforementioned operation and effect of the invention are more apparent. The extension ratio takes on a value relative to the natural length as 100%.

In accordance with an exemplary embodiment of the invention, the absorbent article is an underpants-type disposable diaper including: an outer body that constitutes a front body part and a back body part; and an inner body that is fixed to an inner surface of the outer body and contains an absorber, the front body part and the back body part being joined together at both sides to form side seal portions to form an annular waist portion, an waist opening, and a pair of right and left leg openings, wherein the elastic structure is provided such that the resilient and elastic members are positioned along the width direction in areas of the outer body including at least both sides along the width direction of the inner body.

(Operation and Effect)

The elastic structure in the present invention is suited for the areas of the outer body at least at the both sides along the width direction of the inner body in the underpants-type disposable diaper.

In accordance with an exemplary embodiment of the invention, the areas of the outer body at the both sides along the width direction of the inner body are divided into end areas at the inner body side, end areas at the side seal portion side, and intermediate areas between the former areas, and spacing between sheet joined sections in at least one of the end areas at the inner body side and the end areas at the side seal portion side is narrower than spacing between sheet joined sections in the intermediate areas.

(Operation and Effect)

When the sheet joined sections are intermittently provided in the extending direction, the fixing force of the resilient and elastic members becomes inevitably lowered, and the resilient and elastic members may come off. In particular, the width of the sheet joined sections is desirably narrow in the extending direction, but in this case, the resilient and elastic members and the sheet joined sections intersect each other at smaller points. That is, the resilient and elastic members need to be fixed in the smaller points. It is thus important to assure the fixing force of the resilient and elastic members. Accordingly, as described above, it is desired that the spacing between the sheet joined sections in the end areas is narrower than the spacing between the sheet joined sections in the intermediate areas to reinforce the fixing.

In accordance with an exemplary embodiment of the invention, when the areas of the outer body at the both sides along the width direction of the inner body are divided into end areas at the inner body side, end areas at the side seal portion side, and intermediate areas between the former areas, a fixed width of the resilient and elastic members in at least one of the end areas at the inner body side and the end areas at the side seal portion side is larger than a fixed width of the resilient and elastic members in the intermediate areas.

(Operation and Effect)

When the sheet joined sections are intermittent in the extending direction, the fixing force of the resilient and elastic members becomes inevitably lowered, and the resilient and elastic members may come off. In particular, the width of the sheet joined sections is desirably narrow in the extending direction. In this case, however, the resilient and elastic members and the sheet joined sections intersect each other at smaller points. The resilient and elastic members need to be fixed in the smaller points, and it is thus important to assure the fixing force of the resilient and elastic members. Accordingly, as described above, it is desired that the fixed width of the resilient and elastic members in the end areas is larger than the fixed width of the resilient and elastic members in the intermediate areas to reinforce the fixing.

In an accordance with an exemplary embodiment of the invention, a method for manufacturing an elastic structure for absorbent article is disclosed, in which the absorbent article includes a first sheet material having a surface to be in contact with a wearer's skin; a second sheet material stuck to a surface of the first sheet material opposite to the surface to be in contact with the wearer's skin; and a plurality of resilient and elastic members that is provided between the first sheet material and the second sheet material along an extending direction with spacing therebetween, wherein an adhesive is applied to the surface of the first sheet material at the second sheet material side intermittently in the extending direction and continuously in a direction intersecting with the extending direction, no adhesive is applied to the surface of the second sheet material at the first sheet material side, the resilient and elastic members are sandwiched in an elongated state between the first sheet material and the second sheet material, the first sheet material and the second sheet material are joined together by the adhesive, and the first sheet material and the resilient and elastic members are joined together by the adhesive.

(Operation and Effect)

By the invention of the disclosed method, the disclosed elastic structure can be manufactured.

Advantageous Effects of Invention

As described above, the present invention produces advantages that the absorbent article has the ridges extended in a straight line with excellent in appearance and air permeability, and provides excellent fluffy feel, and others.

DESCRIPTION OF EMBODIMENTS

Embodiments of the present invention will be described below with reference to the accompanying drawings.

FIGS. 1 to 8 illustrate one example of underpants-type disposable diaper 100. The underpants-type disposable diaper 100 is composed of an outer body 12 constituting the outer surface (back surface) of the product and an inner body 200 stuck to the inner surface of the outer body 12. Reference sign Y indicates the entire length of the diaper, and reference sign X indicates the entire width of the diaper.

The inner body 200 is a portion absorbing and retaining excretion such as urine, and the outer body 12 is a portion for attaching the diaper to the wearer. The dotted portions in the cross-sectional views indicate joined sections where constituent members are joined together. The joined sections are formed by application of a hot-melt adhesive through solid, bead, curtain, summit, or spiral coating. In the following description, the "front-back direction" refers to the direction linking the ventral side (front side) and the back side (rear side), and the "width direction" refers to the direction (right-left direction) orthogonal to the front-back direction. The "up-down" direction refers to the direction that becomes orthogonal to the waist direction when the diaper 100 is worn, that is, when the diaper 100 is folded into two at the crotch portion such that the front body part and the back body part are overlapped at the both sides, in other words, the direction linking a waist opening WO and a crotch portion.

(Inner Body)

Figure 3:
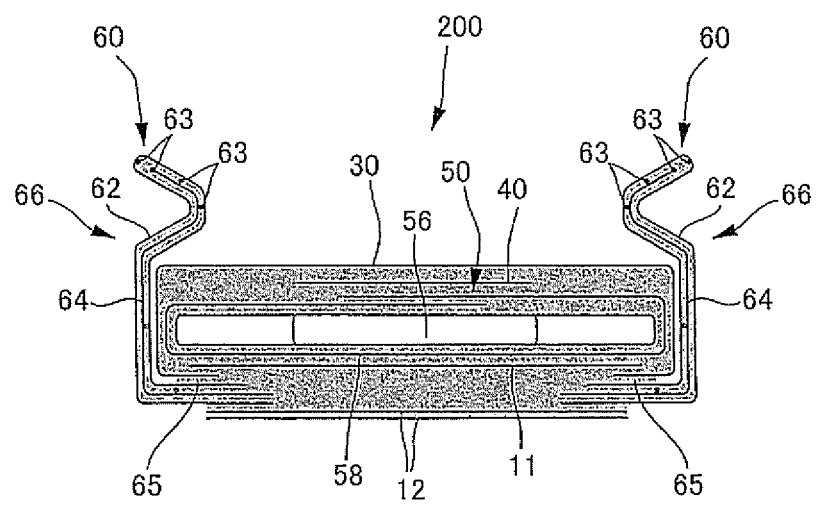
FIG. 3 is a cross-sectional view of FIG. 1 taken along line 3-3.
Figure 4:
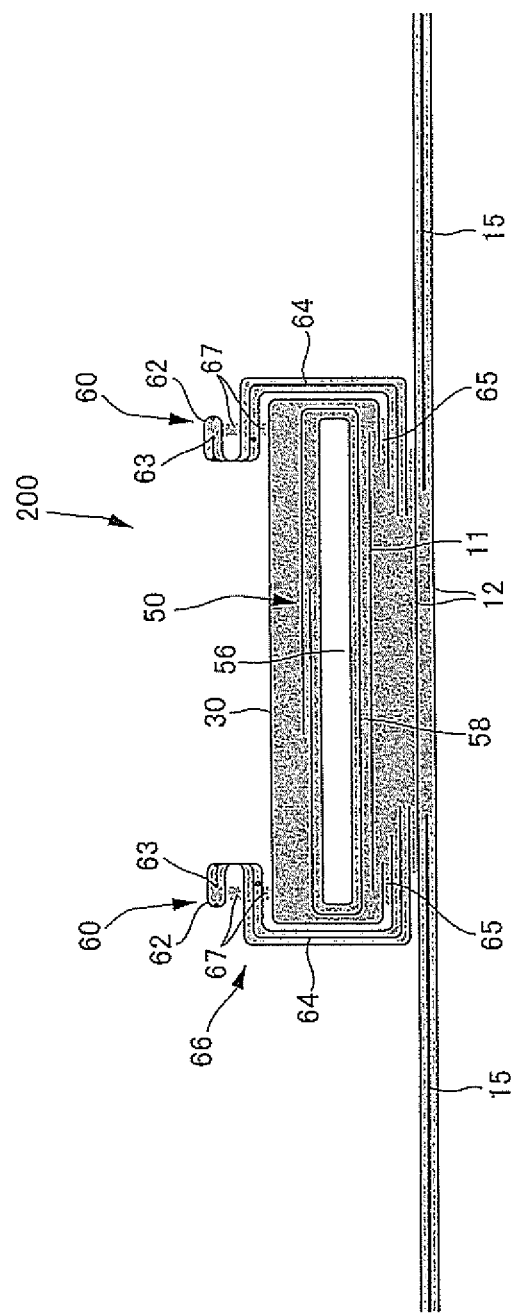
FIG. 4 is a cross-sectional view of FIG. 1 taken along line 4-4.
Figure 5:
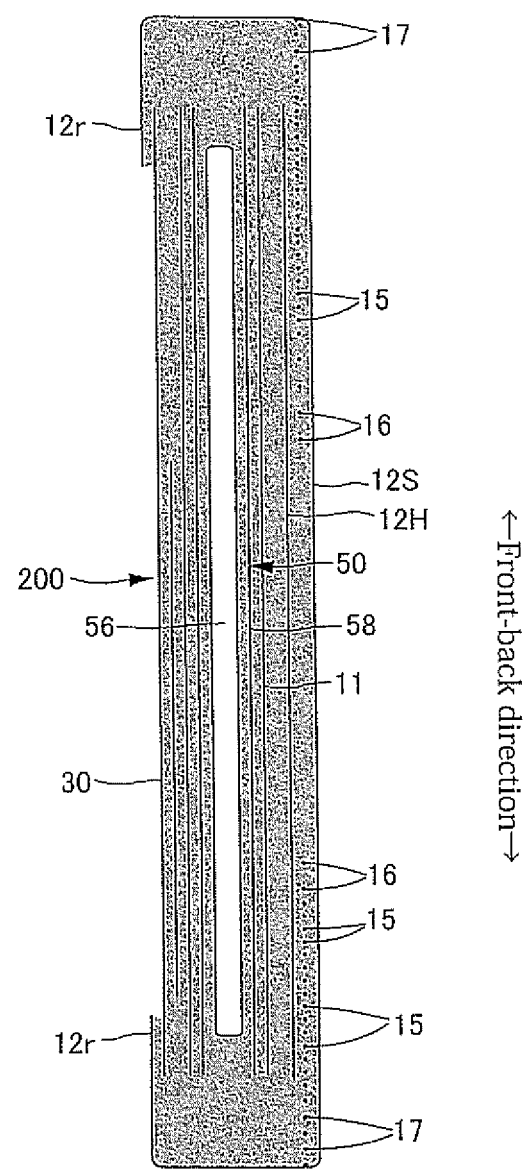
FIG. 5 is a cross-sectional view of FIG. 1 taken along line 5-5.

The inner body 200 may be formed in any shape although it is rectangular in the drawings. The inner body 200 is a main body part with absorptive function that includes a face sheet 30 on the wearer's body side, a liquid impervious sheet 11, and an absorbent element 50 intervening between these sheets as illustrated in FIGS. 3 to 5. Reference sign 40 indicates an interlayer sheet (second sheet) provided between the face sheet 30 and the absorbent element 50 to move quickly the liquid having passed through the face sheet 30 to the absorbent element 50. Reference sign 60 indicates three-dimensional gathers 60 standing from the both sides of the inner body 200 toward the wearer's body to prevent excretion from leaking toward the both sides of the inner body 200.

(Face Sheet)

The face sheet 30 is pervious to liquid and may be a porous or non-porous non-woven fabric sheet or a porous plastic sheet, for example. There is no specific limitation on raw fibers for the non-woven fabric. For example, the raw fibers may be synthetic fibers based on olefin such as polyethylene or polypropylene, polyester, polyamide, or reproduced fibers of rayon or cupra, natural fibers of cotton or the like, mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example. For flexibility and drape properties, spun-bonding and spun-lacing are preferred. For bulkiness and softness, air-through processing, point-bonding, and thermal bonding are preferred.

The face sheet 30 may be composed of a single sheet or a layered sheet obtained by sticking two or more sheets to each other. Similarly, the face sheet 30 may be composed of a single sheet or two or more sheets in a planar direction.

In the case of providing the three-dimensional gathers 60, it is preferred that the both sides of the face sheet 30 are extended up to the back side of the absorbent element 50 between the liquid impervious sheet 11 and the three-dimensional gathers 60, and are adhered to the liquid impervious sheet 11 and the three-dimensional gathers 60 by a hot-melt adhesive or the like to prevent liquid penetration.

(Interlayer Sheet)

To move the liquid having passed through the face sheet 30 quickly to the absorber, the interlayer sheet (called also second sheet) 40 higher in liquid permeation speed than the face sheet 30 may be provided. The interlayer sheet 40 can not only move the liquid quickly to the absorber with enhancement in absorption performance of the absorber but also prevent a "back-flow" phenomenon of the absorbed liquid from the absorber to keep the face sheet 30 in a dry state. The interlayer sheet 40 may not be provided.

The interlayer sheet 40 may be made from the same material as that for the face sheet 30, or spun-laced, spun-bonded, SMS, or pulp non-woven fabric, or mixture of pulp and rayon, point-bonded or crape paper, for example. In particular, air-through non-woven fabric is preferred due to its bulkiness. The air-through non-woven fabric preferably uses composite fibers of core-sheath structure. The resin for the core is acceptably polypropylene (PP) but preferably polyester (PET) due to high rigidity. The basis weight of the fiber is preferably 20 to 80 $g/m^2$, more preferably 25 to 60 $g/m^2$. The fineness of raw fibers for the non-woven fabric is preferably 2 to 10 dtex. To increase the bulk of the non-woven fabric, all or some of the raw fibers are preferably eccentric fibers with cores not centered, hollow fibers, or eccentric and hollow fibers.

The interlayer sheet 40 in the illustrated example is centered on an absorber 56 and is narrower than the absorber 56. Alternatively, the interlayer sheet 40 may be provided over the entire width of the absorber 56. The interlayer sheet 40 may be the same in length as the absorber 56, or may be shorter than the absorber 56, falling within the central area for receiving the liquid.

(Liquid Impervious Sheet)

There is no particular limitation on the material for the liquid impervious sheet 11. For example, the liquid impervious sheet 11 may be a plastic film made from an olefin resin such as polyethylene or polypropylene, a laminate non-woven fabric sheet with a plastic film on the surface of non-woven fabric, a layered sheet in which non-woven fabric is laid on a plastic film, or the like. The liquid impervious sheet 11 is preferably made from a liquid-impervious and moisture-pervious material that has been favorably used in recent years for the viewpoint of prevention of stuffiness. As a widely used moisture-pervious plastic film, there is a microporous plastic film that is obtained by melting and kneading an inorganic filling agent in an olefin resin such as polyethylene, polypropylene, or the like, for example, to form a sheet and then elongating the sheet in a uniaxial or biaxial direction. Besides, the liquid impervious sheet 11 may be a non-woven fabric sheet of microdenier fibers, or may be a liquid-impervious sheet that is formed without the use of a plastic film, by enhancing leak-proof performance by reducing the size of gaps between fibers with the application of heat or pressure or by coating the sheet with a high-water absorption resin, a hydrophobic resin, or a water repellent agent.

For enhancement of leak-proof performance, the liquid impervious sheet 11 is preferably extended through the both sides of the absorbent element 50 to the both sides of the absorbent element 50 at the face sheet 30 side. The appropriate width of the extended portions is about 5 to 20 mm at each of the right and left sides.

An excretion indicator changed in color by absorption of liquid may be provided at the inside of the liquid impervious sheet 11, in particular, on the side surfaces of the absorber 56.

(Three-Dimensional Gathers)

The three-dimensional gathers 60 are belt-shaped members extended entirely along the both sides of the inner body 200 in the front-back direction. The three-dimensional gathers 60 are provided to shut off urine or loose stool moving laterally over the face sheet 30 to prevent lateral leakage of the liquid. In this embodiment, the three-dimensional gathers 60 stand on the sides of the inner body 200. Each of the three-dimensional gathers 60 stands obliquely toward the central portion in the width direction at the base side, and stands obliquely toward the outside in the width direction from the middle portion to the edge portion.

More specifically, each of the three-dimensional gathers 60 is formed such that a belt-shaped gather sheet 62 having the same length as the length of the inner body 200 in the front-back direction is folded back in two in the width direction, and a plurality of elongated resilient and elastic members 63 is fixed in an elongated state along the longitudinal direction at spacing therebetween in the width direction between the sheets at the folded portion and its neighborhood. The end portions of the three-dimensional gathers 60 at the sides opposite to the folded portions in the width direction constitute attachment portions 65 fixed to the back surface of the inner body 200 at the side edges. The portions of the three-dimensional gathers 60 other than the attachment portions 65 constitute protrusions 66 (folded portion side portions) that protrude from the attachment portions 65. The both ends of the protrusions 66 in the front-back direction include base portions that are extended from the attachment portions 65 through the sides of the inner body 200 to the side surfaces of the face sheet 30 and are fixed by front-back fixed portions 67 with a hot-melt adhesive or a heat seal to the side surfaces of the face sheet 30, and edge portions that are folded back from the edges of the base portions toward the outside in the width direction and are fixed to the base portions. The middle portions of the protrusions in the front-back direction are non-fixed free portion (inner free portions) to which the elongated resilient and elastic members 63 are fixed in an elongated state along the front-back direction.

The gather sheet 62 may be preferably formed by applying a water repellent treatment with silicon or the like as necessary to flexible non-woven fabric excellent in uniformity and concealing performance such as spun-bonded non-woven fabric (SS, SSS, or the like), SMS non-woven fabric (SMS, SSMMS, or the like), or melt-blown non-woven fabric. The basis weight of the fibers is preferably about 10 to 30 g/m$^2$. The elongated resilient and elastic members 63 may be rubber threads or the like. In the case of using spandex rubber threads, the fineness of the threads is preferably 470 to 1240 dtex, more specifically 620 to 940 dtex. The extension ratio of the threads at the time of fixing is preferably 150 to 350%, more specifically 200 to 300%. The "extension ratio" herein takes on a value relative to the natural length as 100%. In addition, a water-proof film 64 may intervene in the gather sheet folded in two as illustrated in the drawing.

The number of the elongated resilient and elastic members 63 provided in the free portions of the three-dimensional gathers 60 is preferably two to six, more specifically three to five. The arrangement interval 60d is appropriately 3 to 10 mm. According to this configuration, the diaper is likely to touch the skin by surface with arrangement of the elongated resilient and elastic members 63. The elongated resilient and elastic members 63 may be arranged not only at the edge portions but also at the base portions.

The attachment portions 65 of the three-dimensional gathers 60 may be fixed to appropriate members in the inner body 200 such as the face sheet 30, the liquid impervious sheet 11, and the absorbent element 50.

In the thus configured three-dimensional gathers 60, the contraction force of the elongated resilient and elastic members 63 acts to make the both end portions in the front-back direction closer to each other. The both end portions of the protrusions 66 in the front-back direction are fixed so as not to stand, whereas the middle portions between the both ends of the protrusions 66 are non-fixed free portions. Accordingly, only the free portions stand to touch the wearer's body as illustrated in FIG. 3. In particular, when the attachment portions 65 are positioned on the back surface of the inner body 200, the three-dimensional gathers 60 stand and open outward in the width direction at the crotch portion and its neighborhood. Accordingly, the three-dimensional gathers 60 are brought into surface contact with the circumferences of the legs to produce an improved fit.

Figure 7:
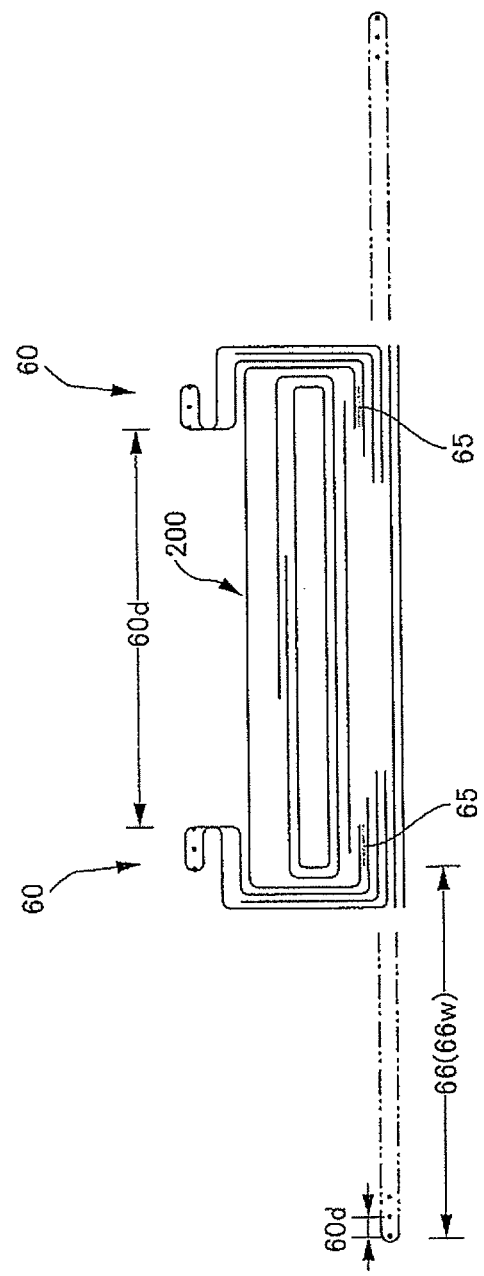
FIG. 7 is a cross-sectional view of main parts of the underpants-type disposable diaper.

The dimensions of the three-dimensional gathers 60 can be decided as appropriate. In the case of a disposable diaper for infants, however, the standing height 66w of the three-dimensional gathers 60 (width of the protrusions 66 in an open state) is 15 to 60 mm, more specifically 20 to 40 mm as illustrated in FIG. 7, for example. In addition, the separation distance 60d between the folds at the innermost side in the flatly folded state is 60 to 190 mm, more specifically 70 to 140 mm, to make the three-dimensional gathers 60 parallel to the surface of the face sheet 30.

Unlike in the illustrated example, the three-dimensional gathers may be provided doubly (in two rows) at each of the right and left sides of the inner body 200.

(Absorbent Element)

The absorbent element 50 has the absorber 56 and a wrapping sheet 58 for wrapping the entire absorber 56. The wrapping sheet 58 may not be provided.

(Absorber)

The absorber 56 may be formed from a fiber assembly. The fiber assembly may be fluff pulp fibers or accumulated short fibers such as synthetic fibers, or a filament assembly obtained, as necessary, by opening tows (fiber bundles) of synthetic fibers such as cellulose acetate. The basis weight of fluffy pulp or accumulated short fibers may be about 100 to 300 g/m$^2$, and the basis weight of a filament assembly may be about 30 to 120 g/m$^2$, for example. The fineness of synthetic fibers is 1 to 16 dtex, for example, preferably 1 to 10 dtex, more preferably 1 to 5 dtex. In the case of a filament assembly, the filaments may be non-crimped fibers but are preferably crimped fibers. The number of crimps in the crimped fibers may be about 5 to 75 per inch, preferably 10 to 50 per inch, more preferably about 15 to 50 per inch. The crimped fibers are evenly crimped in many cases. High-absorbent polymer particles are preferably dispersed and held in the absorber 56.

Figure 1:
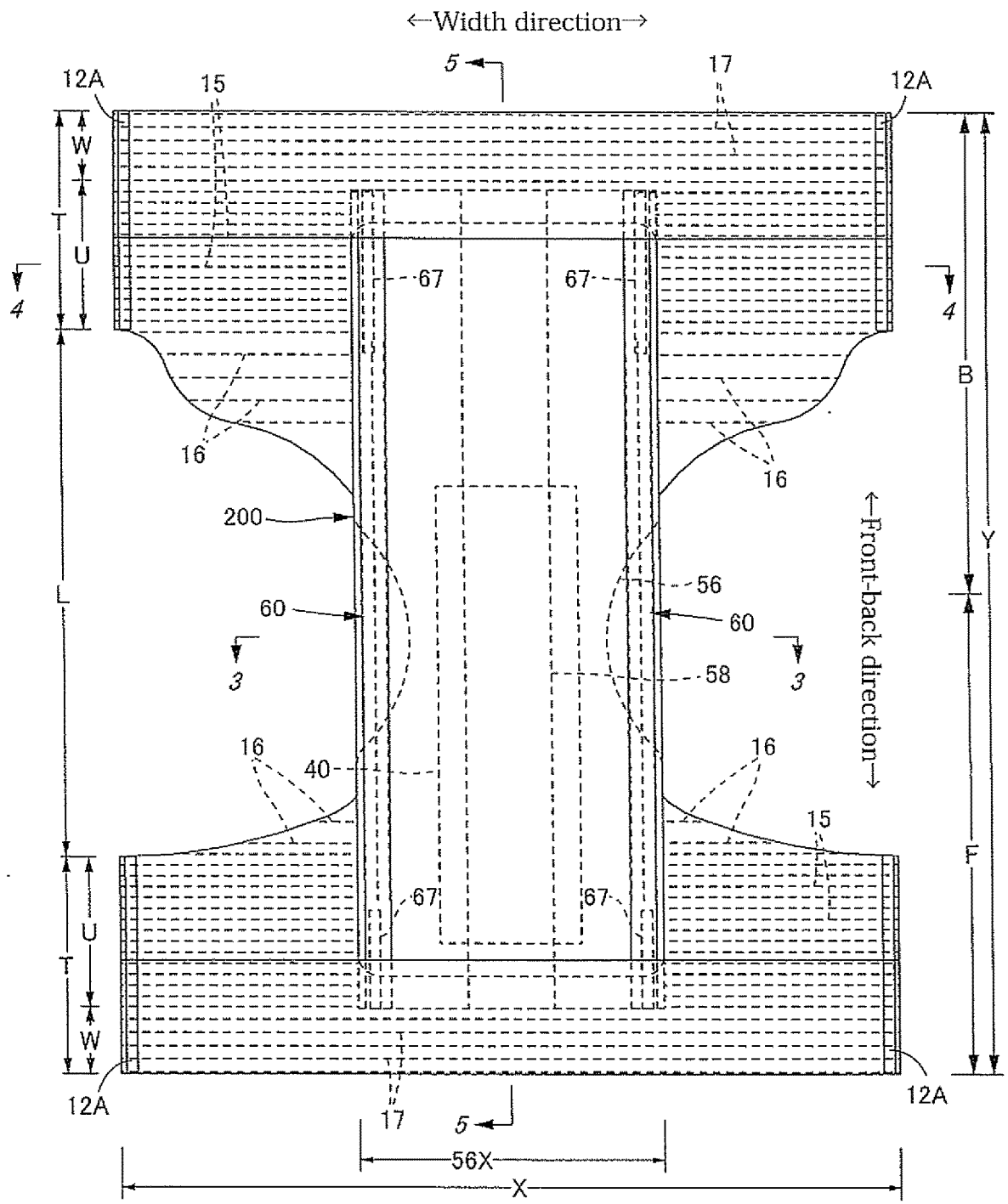
FIG. 1 is a planar view of an inner surface of an underpants-type disposable diaper in an open state.
Figure 2:
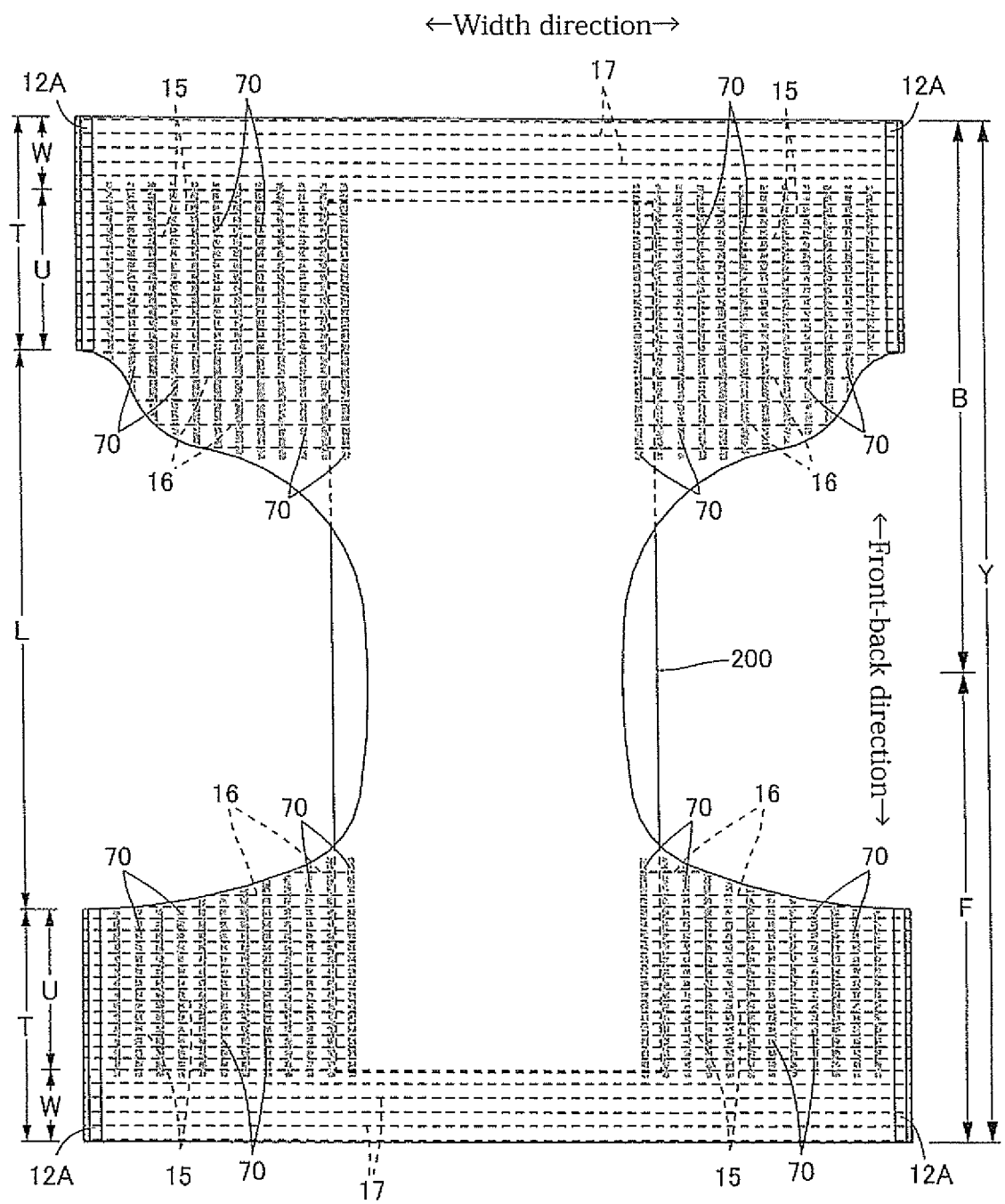
FIG. 2 is a planar view of an outer surface of the underpants-type disposable diaper in an open state.

The absorber 56 may be rectangular in shape but preferably has a hourglass shape having a front end portion, a back end portion, and a narrower portion that is positioned between the front and back end portions and is narrower than the two end portions as illustrated in FIG. 1 to improve the absorber 56 and the three-dimensional gathers 60 in a fit to the circumferences of the legs.

The dimensions of the absorber can be decided as appropriate. Nevertheless, the absorber preferably extends to the peripheral edges of the inner body or their neighborhoods in the front-back direction and the width direction. Reference sign 56X indicates the width of the absorber 56.

(High-Absorbent Polymer Particles)

The absorber 56 may partially or entirely contain high-absorbent polymer particles. The high-absorbent polymer particles include "particles" and "powder". The diameter of the high-absorbent polymer particles may be the same as that of the particles for general use in this type of absorbent article, and is desirably 1000 μm or less, in particular 150 to 400 μm. There is no particular limitation on the material for the high-absorbent polymer particles but the material preferably has a water absorbing capability of 40 g/g or more. The high-absorbent polymer particles may be based on starch, cellulose, or synthetic polymer. The high-absorbent polymer particles may be made of a starch-acrylic acid (acrylate) graft copolymer, a saponified material of starch-acrylonitrile copolymer, a crosslinking substance of carboxymethyl-cellulose sodium, an acrylate polymer, or the like. The high-absorbent polymer particles are preferably used in a general particulate form but may be used in another form.

The water-absorbing speed of the high-absorbent polymer particles is preferably 40 seconds or less. At a water-absorbing speed of more than 40 seconds, the absorbed liquid is more likely to flow back from the absorber 56 to the outside of the absorber 56 (so called "back-flow").

The gel strength of the high-absorbent polymer particles is preferably 1000 Pa or more. Accordingly, it is possible to suppress effectively a sticky feeling of the absorber 56 after liquid absorption even when the absorber 56 is of high bulk.

The basis weight of the high-absorbent polymer particles can be decided as appropriate according to the absorbing capability required for the use of the absorber 56. Although not definitely specified, the basis weight may be 50 to 350 g/m$^2$. When the basis weight of the polymer is less than 50 g/m$^2$, it is difficult to provide the necessary absorbing capability. When the basis weight of the polymer exceeds 350 g/m$^2$, the absorbing effect becomes saturated.

If necessary, the high-absorbent polymer particles can be adjusted in dispersing density or dispersing quantity along the planar direction of the absorber 56. For example, the dispersing quantity of the high-absorbent polymer particles may be larger in the excretion area than the other areas. With regard to gender differences, the dispersing density (quantity) of the high-absorbent polymer particles may be increased at the front side of the product for male, and may be increased at the central part of the product for female. In addition, the polymer may not be provided locally (e.g. in spots) in the absorber 56 in the planar direction.

(Wrapping Sheet)

In the case of using the wrapping sheet 58, its material may be tissue paper, in particular, crape paper, non-woven fabric, polyethylene-laminated non-woven fabric, a porous sheet, or the like. However, the material sheet is desirably configured to retain the high-absorbent polymer particles. In the case of using non-woven fabric instead of crape paper, the hydrophilic SMS non-woven fabric (SMS, SSMMS, or the like) is preferred in particular and its material may be polypropylene, polyethylene/polypropylene composite, or the like. The basis weight of the material is desirably 5 to 40 g/m$^2$, in particular 10 to 30 g/m$^2$.

The form of wrapping by the wrapping sheet 58 can be decided as appropriate. Nevertheless, from the viewpoint of ease of manufacture and prevention of leakage of the high-absorbent polymer particles from the front and back end edges, the wrapping sheet 58 preferably wraps the absorber 56 in a cylindrical form to surround the front and back surfaces and both side surfaces of the absorber 56, and has front and back edges extended off from the front and back sides of the absorber 56 so that the extended portions are crushed on the front and back sides and joined together by a joint means such as a hot-melt adhesive.

(Outer Body)

Figure 8:
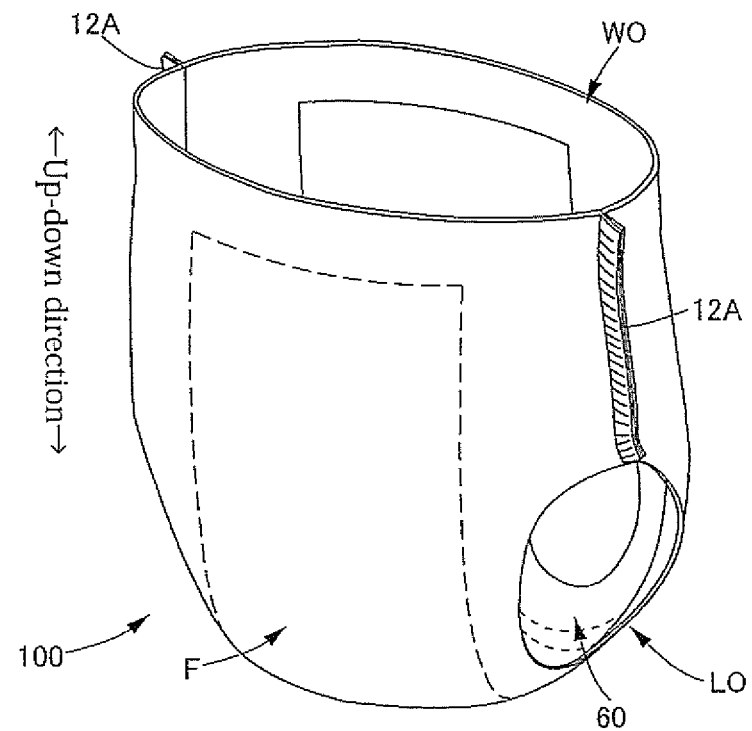
FIG. 8 is a perspective view of the underpants-type disposable diaper.

The outer body 12 has a part constituting a front body part F extended from the crotch portion to the ventral side and a part constituting a back body part B extended from the crotch portion to the back side. The front body part F and the back body part B are joined together at the both sides to form a waist opening WO through which the wearer's waist is passed and a pair of right and left leg openings LO through which the wearer's legs are passed, as illustrated in FIG. 8. Reference sign 12A indicates joining portions (hereinafter, also referred to as side seal portions). The crotch portion refers to a central portion in the front-back direction from the waist edge of the front body part F to the waist edge of the back body part B in an open state. The portions on the front side and the back side of the crotch portion refer to the front body part F and the back body part B, respectively.

The outer body 12 has waist portions T determined as front-back areas from the waist opening WO to the upper ends of the leg openings LO, and an intermediate portion L determined as a front-back area forming the leg openings LO (between the front-back area having the side-seal-portions 12A of the front body part F and the front-back area having the side seal portions 12A of the back body part B). The waist portions T are conceptually divided into "waist edge portions" W forming the edge of the waist opening and "waist lower portions" U as the portions under the waist edge portions W. The lengths of these portions in the vertical direction vary depending on the size of the product and can be decided as appropriate. As an example, the length of the waist edge portions W may be 15 to 40 mm, and the length of the waist lower portion U may be 65 to 120 mm. The both side edges of the intermediate portion L are narrowed along the circumferences of the wearer's legs, and the wearer's legs are placed through the narrowed side edges. As a result, the outer body 12 has an almost hourglass shape as a whole. The degree of narrowing of the outer body 12 can be decided as appropriate. As in the modes illustrated in FIGS. 1 to 8, the outer body 12 is preferably narrower than the inner body 200 at the narrowest area for simple appearance. Alternatively, the outer body 12 may be wider than the inner body 200 even at the narrowest area.

The outer body 12 is formed by joining the two sheet materials 12S and 12H as illustrated in FIGS. 3 to 6. The second sheet material 12H positioned inside extends up to the edge of the waist opening WO, whereas the first sheet material 12S positioned outside wraps around the edge of the second sheet material 12H at the waist side and folds back toward the inside. Folded portions 12*r* are extended to cover the upper end portion of the inner body 200 at the waist side.

There is no particular limitation on the sheet materials 12S and 12H as far as they are formed in sheet form, but they are preferably made from non-woven fabric. There is no specific limitation on raw fibers for the non-woven fabric. For example, the raw fibers may be synthetic fibers based on olefin such as polyethylene or polypropylene, polyester, polyamide, or reproduced fibers of rayon or cupra, natural fibers of cotton or the like, mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example.

The outer body 12 is provided with elongated resilient and elastic members 15 to 17 such as rubber threads at a predetermined extension ratio between the two sheet materials 12S and 12H to enhance a fit to the wearer's waist. The elongated resilient and elastic members 15 to 17 may be made from synthetic rubber or natural rubber.

More specifically, a plurality of waist edge resilient and elastic members 17 is fixed in an elongated state along the width direction at a predetermined extension ratio with intervals therebetween in the up-down direction in such a manner as to be entirely continuous in the width direction, between the inner surface of the second sheet material 12H and the outer surfaces of the folded portions 12r of the first sheet material 12S at the waist edge portions W of the back body part B and the front body part F. One or more of the waist edge resilient and elastic members 17 in the area adjacent to the waist lower portions U may overlap the inner body 200 or may be provided at the both sides of the middle portion in the width direction overlapping the inner body 200 so as not to overwrap the inner body 200 at the middle portion in the width direction. As the waist edge resilient and elastic members 17, about 3 to 22 rubber threads with a fineness of 155 to 1880 dtex, in particular about 470 to 1240 dtex (this is applied in the case of a synthetic rubber, and in the case of a natural rubber, a cross-section area of 0.05 to 1.5 mm$^2$, in particular about 0.1 to 1.0 mm$^2$) are preferably fixed at an extension ratio of 150 to 400%, in particular about 220 to 320%, and at spacing of 4 to 12 mm. All of the waist edge resilient and elastic members 17 may not be equal in fineness and extension ratio. For example, the resilient and elastic members may be different in fineness and extension ratio between the upper and lower sides of the waist edge portions W.

In the waist lower portions U of the front body part F and the back body part B, a plurality of waist lower portion resilient and elastic members 15 composed of elongated resilient and elastic members is fixed in an elongated state in the width direction at a predetermined extension ratio with spacing therebetween in the up-down direction to be entirely continuous in the width direction, between the outer surface of the second sheet material 12H and the inner surface of the first sheet material 12S at the upper side and both sides of the middle portion in the width direction overlapping the inner body 200 so as not to overlap the inner body 200 at the middle portion in the width direction.

As the waist lower portion resilient and elastic members 15, about 5 to 30 rubber threads with a fineness of 155 to 1880 dtex, in particular about 470 to 1240 dtex (this is applied in the case of a synthetic rubber, and in the case of a natural rubber, a cross-section area of 0.05 to 1.5 mm$^2$, in particular about 0.1 to 1.0 mm$^2$) are preferably fixed at an extension ratio of 200 to 350%, in particular about 240 to 300%, and at spacing of 1 to 15 mm, in particular 3 to 8 mm.

In the intermediate portion L of the front body part F and the back body part B between the outer surface of the second sheet material 12H and the inner surface of the first sheet material 12S, a plurality of intermediate portion resilient and elastic members 16 composed of elongated resilient and elastic members is fixed in an elongated state along the width direction at a predetermined extension ratio with spacing therebetween in the up-down direction to be entirely continuous in the width direction at the both sides of the middle portion in the width direction overlapping the inner body 200 so as not to overwrap the inner body 200 at the middle portion in the width direction.

As the intermediate portion resilient and elastic members 16, about 2 to 10 rubber threads with a fineness of 155 to 1880 dtex, in particular about 470 to 1240 dtex (this is applied in the case of a synthetic rubber, and in the case of a natural rubber, a cross-section area of 0.05 to 1.5 mm$^2$, in particular about 0.1 to 1.0 mm$^2$) are preferably fixed at an extension ratio of 150 to 300%, in particular about 180 to 260%, and at spacing of 5 to 40 mm, in particular 5 to 20 mm.

When the waist lower portion resilient and elastic members and the intermediate portion resilient and elastic members 15 and 16 are provided at the both sides of the middle portion in the width direction overlapping the inner body 200 so as not to overwrap the inner body 200 at the middle portion in the width direction as illustrated in the drawings, the inner body 200 does not contract more than necessary in the width direction, does not become lumpy with deterioration in appearance, or does not decrease in absorbing performance. The foregoing form includes the form in which the resilient and elastic members reside only at the both sides in the width direction, and the form in which the resilient and elastic members reside crossing over the inner body 200 from one to the other sides in the width direction, but the resilient and elastic members are finely cut and exert no contraction force at the middle portion in the width direction overlapping the inner body 200 (this means that substantially no resilient and elastic members are provided), and thus the contraction force of the resilient and elastic members acts only at the both sides in the width direction. As a matter of course, the arrangement forms of the waist lower portion resilient and elastic members and the intermediate portion resilient and elastic members 15 and 16 are not limited to the foregoing ones. Alternatively, some or all of the waist lower portion resilient and elastic members and the intermediate portion resilient and elastic members 15 and 16 may be provided crossing over the inner body 200 from the one to the other sides in the width direction so that the contraction force acts on the entire waist lower portions U in the width direction.

(Outer Body Separation Structure)

In the foregoing example, the integral outer body 12 covers continuously from the front body part F to the back body part B. Alternatively, the outer body may be discontinued and separated between the ventral side and the back side (not illustrated). In that case, a crotch portion outer body may be stuck to the outer surface of the inner body to cover the portion exposed between the outer body at the ventral side and the outer body at the back side. As the crotch portion outer body, the same material can be used as that for the foregoing outer body.

(Elastic Structure)

Figure 6:
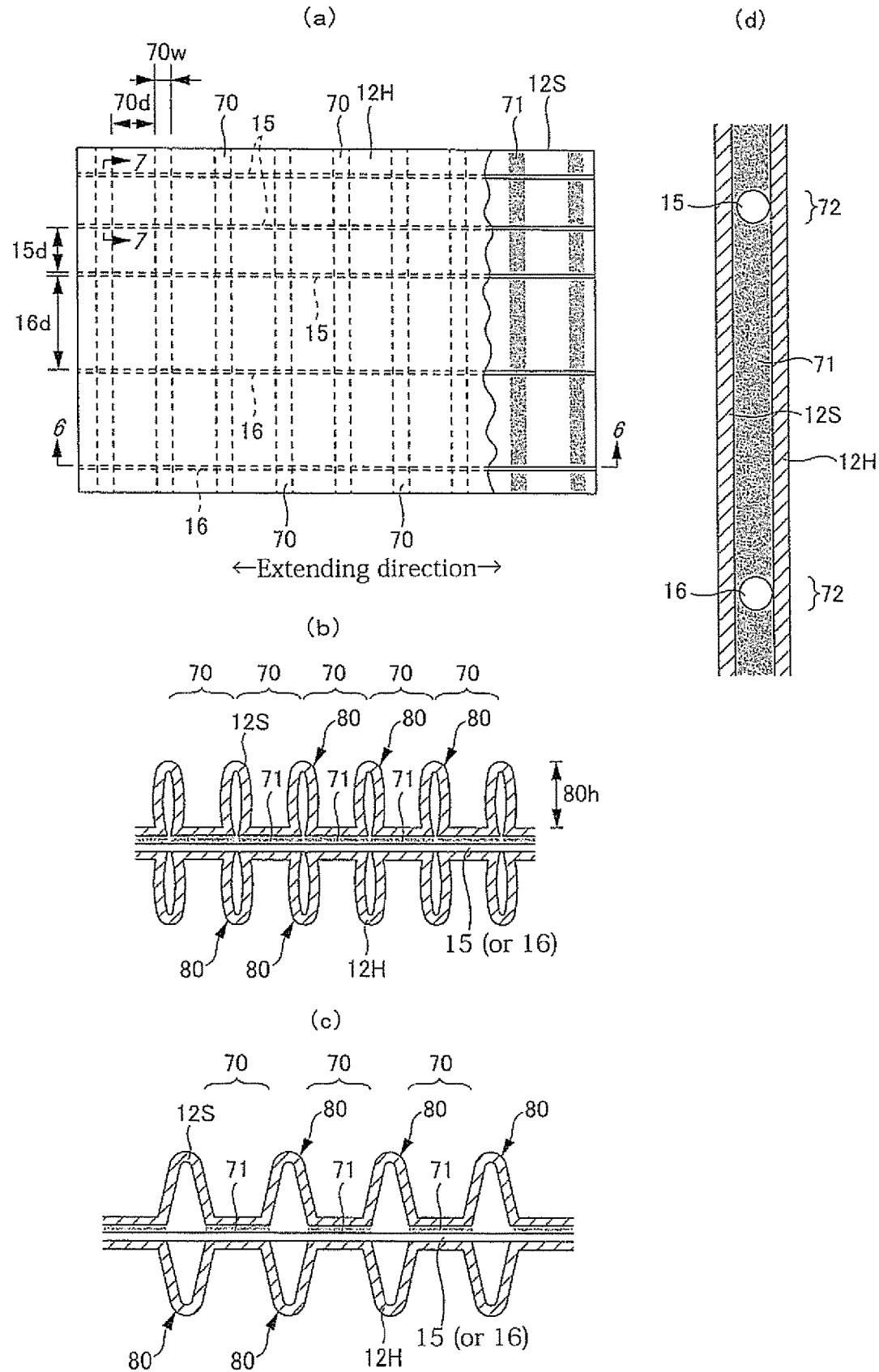
FIG. 6(a) is a planar view of an elastic structure in an open state.
FIG. 6(b) is a cross-sectional view of FIG. 6(a) taken along line 6-6 in a natural length state.
FIG. 6(c) is a cross-sectional view of FIG. 6(a) taken along line 6-6 in a somewhat elongated state.
FIG. 6(d) is a cross-sectional view of FIG. 6(a) taken along line 7-7.

In the underpants-type disposable diaper, an elastic structure of the present invention is employed in the area ranging from the waist lower portions U to the intermediate portion L. Specifically, as illustrated in FIG. 6, the first sheet material 12S and the second sheet material 12H are joined together in the area by an adhesive 71 (a hot-melt adhesive 71 or the like) applied intermittently in the extending direction and continuously with a predetermined width in the direction intersecting with (in the illustrated example, the direction orthogonal to) the extending direction, thereby to form sheet joined sections 70. The sheet joined sections 70 have a width 70w of 0.5 to 4 mm in the extending direction. The adjacent sheet joined sections 70 have a spacing 70d of 4 to 8 mm (preferably 5 to 7 mm) therebetween. The lower limit for the width 70w of the sheet joined sections 70 in the extending direction is preferably 1 mm from the viewpoint of ease of manufacture, and is preferably 0.5 mm from the viewpoint of flexibility. Meanwhile, the upper limit for the width 70w of the sheet joined sections 70 in the extending direction is preferably 2 mm, more preferably 1.5 mm.

There is no particular limitation on the material for the first sheet material 12S and the second sheet material 12H. Nevertheless, they are desirably made from non-woven fabric with a thickness of 0.1 to 1 mm and a basis weight of 10 to 20 g/m$^2$. Each of the first sheet material 12S and the second sheet material 12H may be composed of one non-woven fabric sheet, or either or both of them may be composed of a layered body of plural non-woven fabric sheets.

In particular, it is difficult to assure excellent air permeability, appearance, and fluffy feel of the ridges 80 handled by the present invention, with increase in flexibility of the non-woven fabric. That is, the ridges 80 are thin and prone to be fallen and deteriorated in compression resilience. Accordingly, the structure of the present invention is suited to the case described below. Specifically, the structure of the present invention is suited to the case where at least one of the first sheet material 12S and the second sheet material 12H is made from flexible non-woven fabric such as non-woven fabric of polypropylene (PP) or its copolymer (for example, copolymer mixed with polyethylene or ethylene as a copolymer component) (hereinafter, also referred to as PP-based non-woven fabric), non-woven fabric of core-sheath fibers (PE/PP) with polyethylene (PE) as a sheath and polypropylene (PP) as a core. There is no limitation on the kind of non-woven fabric, but spun-bonded non-woven fabric is preferred for its excellence in strength and flexibility. In particular, spun-bonded non-woven fabric formed by stacking a plurality of spun-bonded layers, for example, SS non-woven fabric (two-layer) or SSS non-woven fabric (three-layer) is more preferably used. Four or more-layer non-woven fabric may be used instead.

The resilient and elastic members 15 and 16 are fixed by the adhesive 71 to at least one of the first sheet material 12S and the second sheet material 12H at the intersections with the sheet joined sections 70. An adhesive different from the adhesive for forming the sheet joined sections may be applied to the resilient and elastic members 15 and 16 or the sheet materials 12S and 12H to fix the resilient and elastic members. In the illustrated example, the adhesive 71 for forming the sheet joined sections 70 is continuously applied in the direction intersecting with the extending direction. Accordingly, the adhesive 71 is used to fix the resilient and elastic members 15 and 16 to at least one of the first sheet material 12S and the second sheet material 12H. At the time of manufacture, the adhesive 71 is applied to one or both of the first sheet material 12S and the second sheet material 12H, and the resilient and elastic members 15 and 16 are sandwiched between the two sheet materials 12S and 12H when the two sheets 12S and 12H are joined together.

In the form illustrated in FIG. 6, the adhesive 71 is applied to the surface of the first sheet material 12S at the second sheet material 12H side, intermittently in the extending direction and continuously with a predetermined width in the direction intersecting with the extending direction, and the adhesive 71 is not applied to the surface of the second sheet material 12H at the first sheet material 12S side, and the resilient and elastic members 15 and 16 are sandwiched in an elongated state between the first sheet material 12S and the second sheet material 12H, and the first sheet material 12S and the second sheet material 12H are joined together by the adhesive 71 and the first sheet material 12S and the resilient and elastic members 15 and 16 are joined together by the adhesive 71. In this case, at the intersections between the sheet joined sections 70 and the resilient and elastic members 15 and 16, the adhesive 71 is continuously applied to the resilient and elastic members 15 and 16 at the first sheet material 12S side in the direction intersecting with the extending direction, and therefore the resilient and elastic members 15 and 16 are fixed to the first sheet material 12S. The adhesive 71 is discontinuously applied to the resilient and elastic members 15 and 16 at the second sheet material 12H side in the direction intersecting with the extending direction. In the drawing, the discontinuous points are illustrated with reference sign 72. The adhesive 71 is intermittently applied to the second sheet material 12H to suppress decrease in flexibility of the second sheet material 12H and also suppress decrease in flexibility of the first sheet material 12S and the second sheet material 12H as a whole. In addition, although the adhesive 71 is continuously applied to the resilient and elastic members 15 and 16 only at the first sheet material 12S side at the intersections with the sheet joined sections 70, the first sheet material 12S and the second sheet material 12H are unified by the sheet joined sections 70 at the both sides of the resilient and elastic members 15 and 16. Accordingly, the contraction force of the resilient and elastic members 15 and 16 acts in a substantially even manner on the first sheet material 12S and the second sheet material 12H to form even ridges in the first sheet material 12S and the second sheet material 12H.

Figure 11:
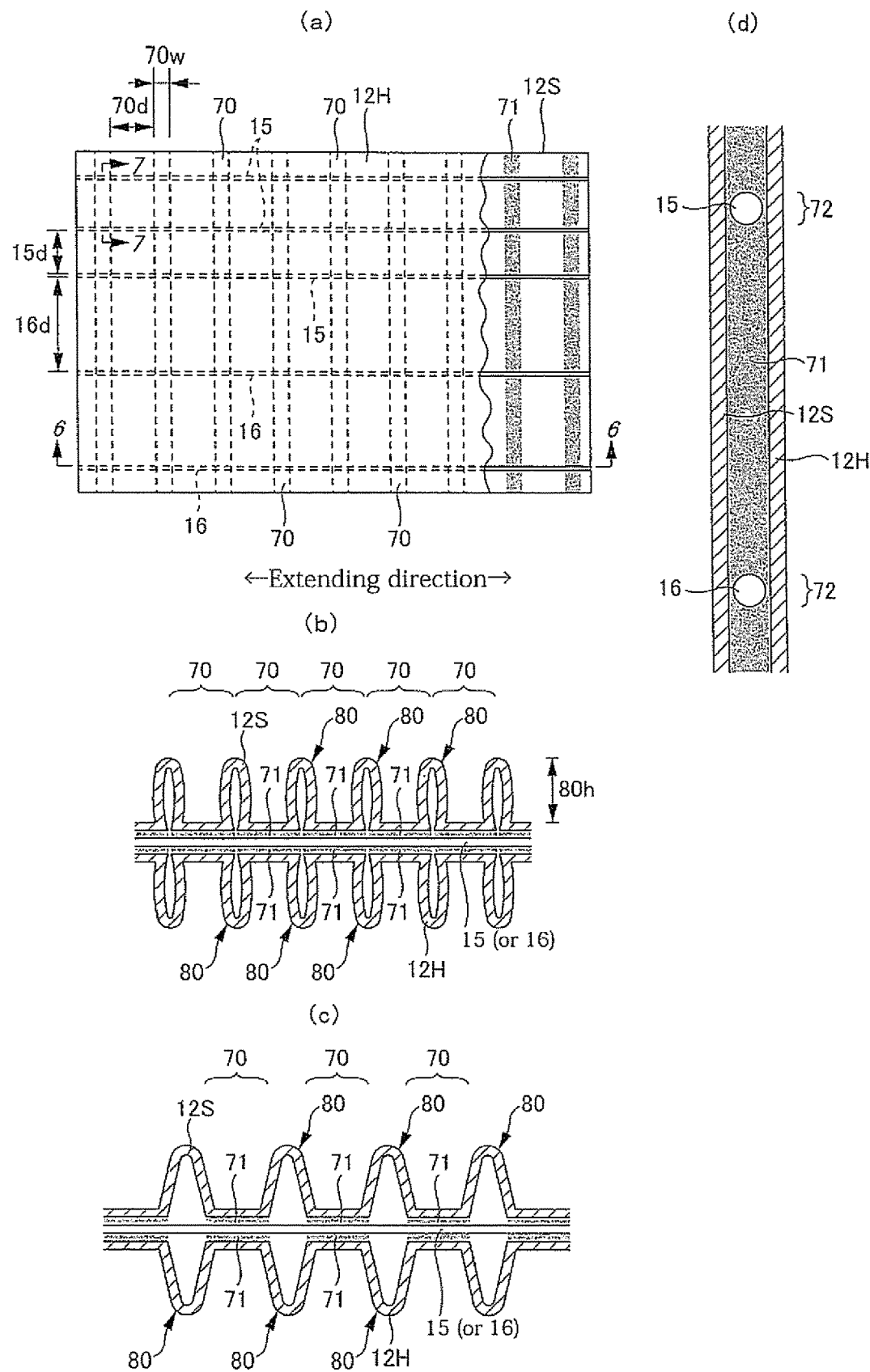
FIG. 11(a) is a planar view of an elastic structure in an open state.
FIG. 11(b) is a cross-sectional view of FIG. 11(a) taken along line 6-6 in a natural length state.
FIG. 11(c) is a cross-sectional view of FIG. 11(a) taken along line 6-6 in a somewhat elongated state.
FIG. 11(d) is a cross-sectional view of FIG. 11(a) taken along line 7-7.

The adhesive 71 may be applied to the first sheet material 12S and the second sheet material 12H in the same pattern. In this case, as illustrated in FIG. 11, at the intersections between the sheet joined sections 70 and the resilient and elastic members 15 and 16, the adhesive 71 is continuously applied with a predetermined width in the direction intersecting with the extending direction to both of the first sheet material 12S side and the second sheet material 12H side of the resilient and elastic members 15 and 16. This produces the advantage that the resilient and elastic members 15 and 16 can be fixed more firmly. Although not illustrated, the resilient and elastic members may be sandwiched and fixed between the first sheet material and the second sheet material with application of the adhesive to the second sheet material and without application of the adhesive to the first sheet material. In these forms, however, the adhesive 71 is continuously applied to the second sheet material 12H and therefore the second sheet material 12H to be contact with the wearer's skin is lowered in flexibility and the area of the second sheet material 12H lowered in flexibility is unfavorably pressed against the wearer's skin. Accordingly, the adhesive 71 is desirably discontinuously applied to the surface of the second sheet material 12H or the like to be in contact with the wearer's skin as in the mode illustrated in FIG. 6.

The adhesive 71 for forming the sheet joined sections 70 is preferably the hot-melt adhesive 71. There is no particular limitation on the kind of the hot-melt adhesive 71. The hot-melt adhesive 71 may be based on EVA, adhesive rubber (elastomer), olefin, polyester polyamide, and the like. The hot-melt adhesive 71 is desirably based on an adhesive rubber (elastomer).

Figure 15:
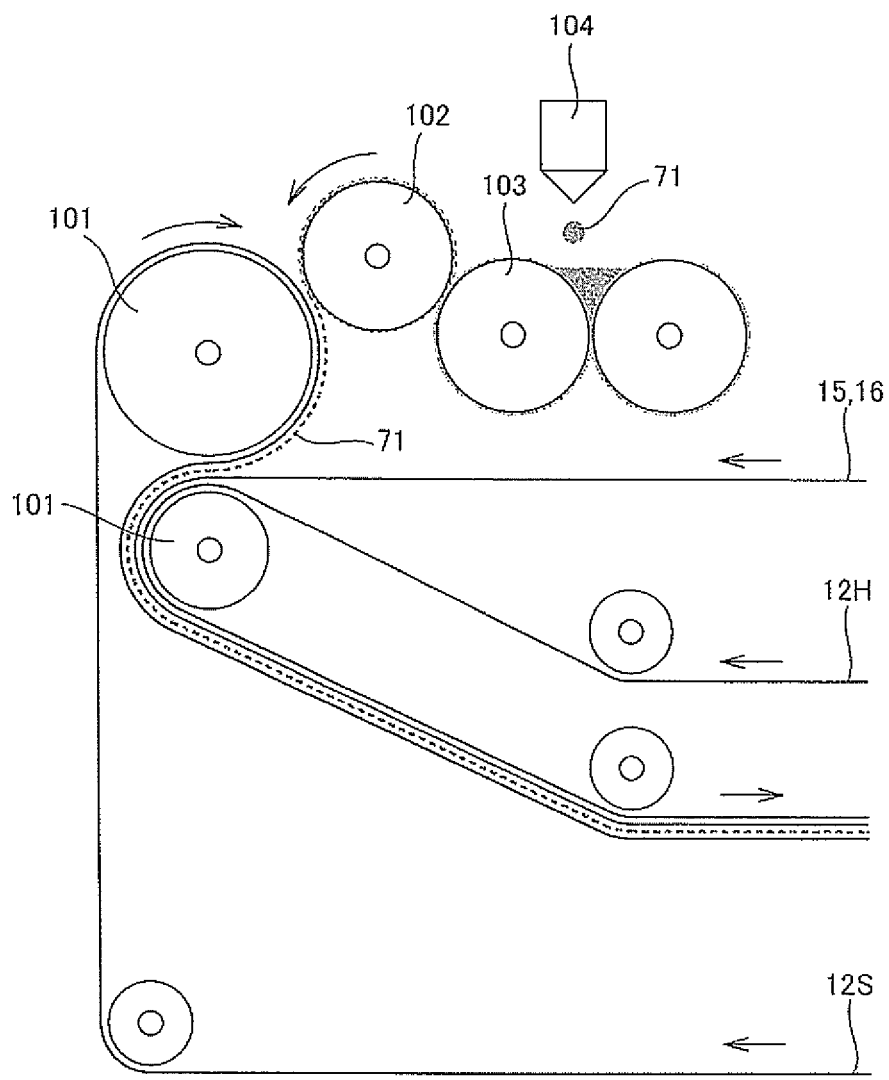
FIG. 15 is a schematic view of adhesion equipment.

There is no particular limitation on the method of application of the hot-melt adhesive 71. However, when the width 70w of the sheet joined sections 70 in the extending direction is narrow, for example, 1 mm or less, the width of application of the hot-melt adhesive also becomes narrow and thus it is difficult to apply the hot-melt adhesive by intermittent coating by spraying from a nozzle such as in the case of curtain or solid coating. Accordingly, it is desired to adopt a pattern coating method suited to narrow-width application (transfer of the hot-melt adhesive 71 by a relief printing technique). FIG. 15 illustrates an example of manufacturing equipment for an elastic structure with the use of pattern coating of the hot-melt adhesive. Specifically, in the example of the pattern-coating manufacturing equipment, the resilient and elastic members 15 and 16 are sandwiched between the second sheet material 12H and the first sheet material 12S with the hot-melt adhesive 71 applied to the surface at the second sheet material 12H side, and these components are fed between a pair of nip rolls 101 and pressed and attached to form the elastic structure illustrated in FIG. 6. Before being fed to the nip rolls 101, the first sheet material 12S is brought into contact with a print roll 102 having a relief pattern intermittent in a circumferential direction to transfer and apply the hot-melt adhesive 71 to the first sheet material 12S intermittently in a conveyance direction (an MD direction parallel to the extending direction) and continuously in a direction (a CD direction) intersecting with the conveyance direction. Reference sign 103 indicates a hot-melt adhesive supply roll (anilox roll in relief printing) for transferring and applying the hot-melt adhesive 71 with a predetermined thickness to the relief pattern on the print roll 102, and reference sign 104 indicates a supply nozzle that supplies the hot-melt adhesive 71 to the hot-melt adhesive supply roll 103.

However, even when the application method with pattern coating is employed, it is considered that some types of hot-melt adhesive 71 become stringy to cause degradation in accuracy of application width (that is, the width of the sheet joined sections 70) and reduction in stability of operation, taking into account the presently general production line speed in Japan. Accordingly, the hot-melt adhesive 71 desirably has a melt viscosity of 10000 mpas or less at a temperature of 140° C., a melt viscosity of 5000 mpas or less at a temperature of 160° C., and a loop tack adhesive force of 2000 g/25 mm or more. This lowers the possibility that the hot-melt adhesive 71 becomes stringy, thereby to improve the accuracy of application width and the stability of operation even at the presently general production line speed in Japan.

The loop tack adhesive force of the hot-melt adhesive 71 is measured in such a manner as described below. That is, the hot-melt adhesive is applied with a thickness of 50 μm to a PET plate with a thickness of 50 μm. The PET plate is cut into a tape 25 mm wide and 125 mm long. The both ends of the tape are overlapped to form a loop. The loop is fixed to an LT-100 loop tack tester (produced by ChemInstruments, Inc.), and then is adhered to a PE (polyethylene) plate in an adhesion area of 25 mm×25 mm in an adhesion time of two seconds. Then, the loop-shaped tape is peeled off from the plate at a temperature of 20° C. at a peeling speed of 300 mm/minute, and the maximum force taken for peeling off the tape is measured and set as loop tack adhesive force.

The melt viscosity of the hot-melt adhesive 71 is measured at a prescribed temperature under JIS Z 8803 standards by the use of a Brookfield B-type viscometer (spindle No. 027).

Figure 12:
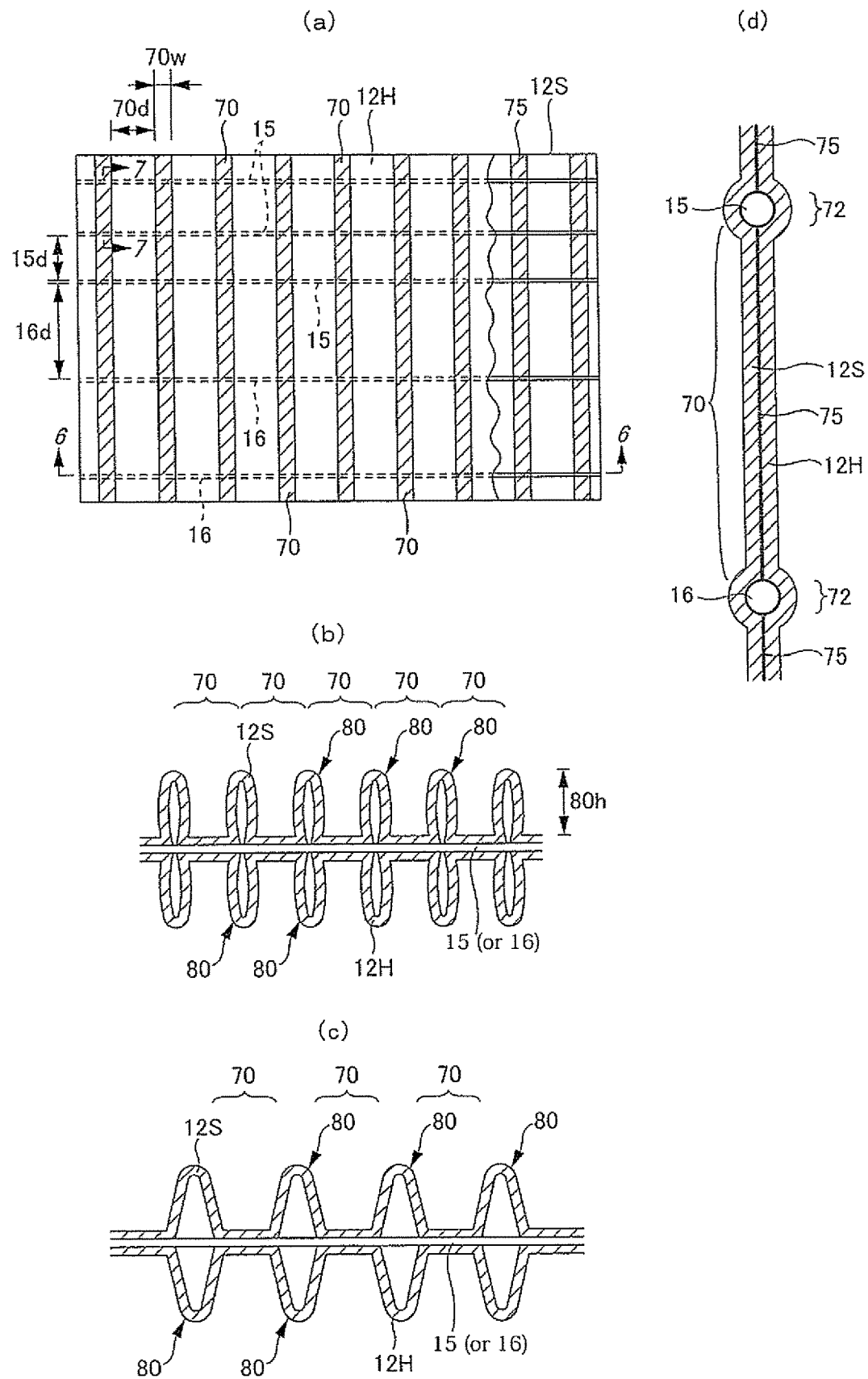
FIG. 12(a) is a planar view of an elastic structure in an open state.
FIG. 12(b) is a cross-sectional view of FIG. 12(a) taken along line 6-6 in a natural length state.
FIG. 12(c) is a cross-sectional view of FIG. 12(a) taken along line 6-6 in a somewhat elongated state.
FIG. 12(d) is a cross-sectional view of FIG. 12(a) taken along line 7-7.

As illustrated in FIG. 12, the sheet joined sections 70 may be formed by a welding process. The welded portions are shown by reference sign 75. The welding process can be performed by any publicly known method such as heat sealing or ultrasonic welding. In this example, the mode in which the welded portions for forming the sheet joined sections 70 are continuously provided includes the mode in which the welded portion are continuously provided because the first and second sheet materials 12S and 12H and the resilient and elastic members 15 and 16 are welded to each other and the first sheet material 12S and the second sheet material 12H are indirectly welded to each other, and the mode in which the welded portions are not continuously provided between the first sheet material 12S and the second sheet material 12H due to the intervention of the resilient and elastic members 15 and 16 at the intersections 72 between the sheet joined sections 70 and the resilient and elastic members 15 and 16, as far as the welded portions are continuously provided on at least one of the first sheet material 12S and the second sheet material 12H. For example, when the resilient and elastic members 15 and 16 are sandwiched between the first sheet material 12S and the second sheet material 12H and the first sheet material 12S and the second sheet material 12H are welded to each other by heat sealing or ultrasonic welding in a continuous pattern crossing over the resilient and elastic members 15 and 16 such that the resilient and elastic members 15 and 16 are not melted but the first sheet material 12S and the second sheet material 12H are melted, the latter mode is implemented because the first and second sheet materials 12S and 12H and the resilient and elastic members 15 and 16 are not welded to each other.

Figure 13:
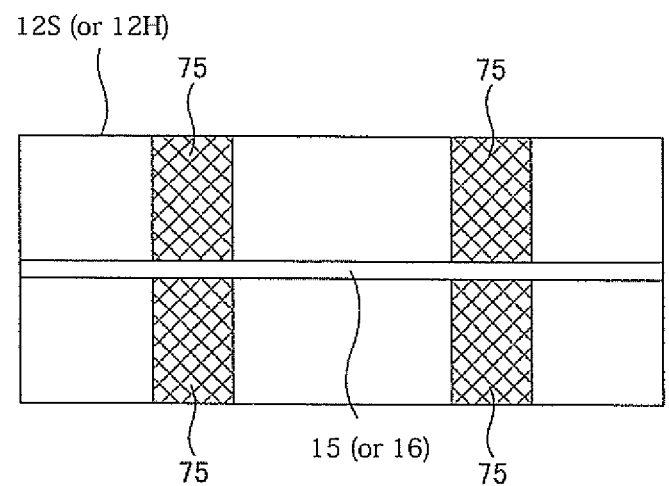
FIG. 13(a) is a planar view of main parts in an elongated state.
FIG. 13(b) is a planer view of the main parts in a contracted state.
Figure 13:
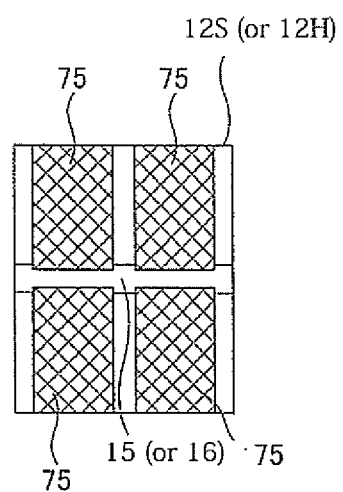
Figure 14:
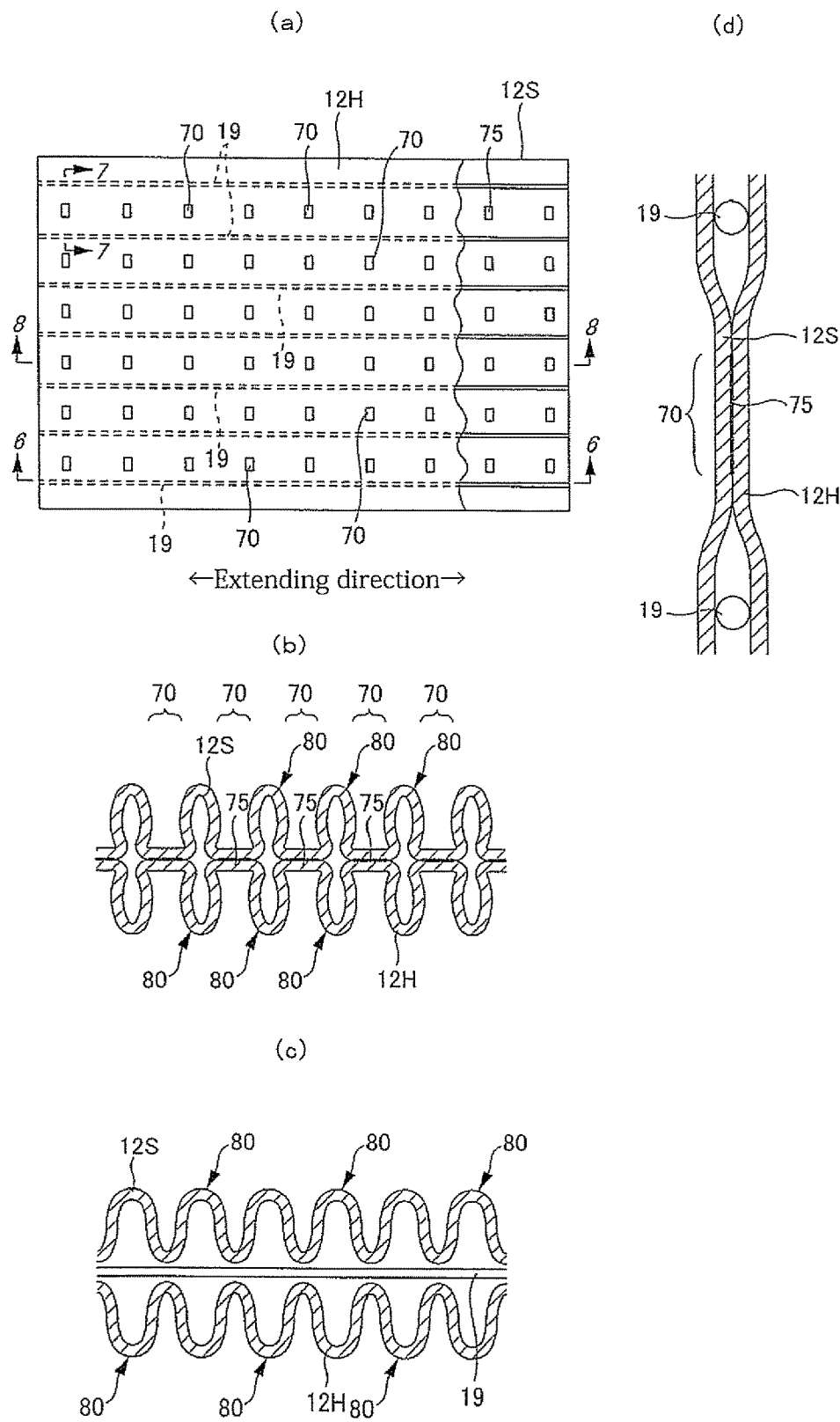
FIG. 14(a) is a planar view of a conventional elastic structure in an open state.
FIG. 14(b) is a cross-sectional view of FIG. 14(a) taken along line 8-8 in a natural length state.
FIG. 14(c) is a cross-sectional view of FIG. 14(a) taken along line 6-6 in a natural length state.
FIG. 14(d) is a cross-sectional view of FIG. 14(a) taken along line 7-7.

The resilient and elastic members 15 and 16 are fixed to at least one of the first sheet material 12S and the second sheet material 12H at the intersections with the sheet joined sections 70. This fixing mode includes the mode in which the resilient and elastic members 15 and 16 and the sheet are adhered to each other (by the adhesive 71 such as a hot-melt adhesive or by a welding process) at the intersections between the resilient and elastic members 15, 16 and the sheet joined sections 70, and the mode in which the resilient and elastic members 15 and 16 and the sheet are not adhered to each other but the spacing between the sheet joined sections 70 in the direction intersecting with the extending direction is smaller than the thickness of the resilient and elastic members 15 and 16 in the natural length state, and the resilient and elastic members 15 and 16 are sandwiched and fixed between the sheet joined sections 70 to transfer the contraction force of the resilient and elastic members 15 and 16 to the sheet at the intersections with the sheet joined sections 70 (refer to JP 2008-154998 A and JP 2009-106667 A). More specifically, the latter mode can be implemented in such a manner that, while the resilient and elastic members 15 and 16 elongated at an extension ratio higher than the extension ratio in the fixed state are sandwiched between the first sheet material 12S and the second sheet material 12H, the sheet joined sections 70 are welded by heat sealing or ultrasonic welding in a continuous pattern crossing over the resilient and elastic members 15 and 16 such that the resilient and elastic members 15 and 16 are not melted but the first sheet material 12S and the second sheet material 12H are melted, and the first sheet material 12S, the second sheet material 12H, and the resilient and elastic members 15 and 16 are not welded together as illustrated in FIG. 13(a), and then the resilient and elastic members 15 and 16 are released from the tension and contracted and increased in diameter, and are sandwiched between the sheet joined sections 70 as illustrated in FIG. 13(b). Accordingly, in the manufactured resultant elastic structure, the welded portions are continuously provided on at least one of the first sheet material 12S and the second sheet material 12H, but the welded portions are not continuously provided between the first sheet material 12S and the second sheet material 12H due to the intervention of the resilient and elastic members 15 and 16 at the intersections between the sheet joined section 70 and the resilient and elastic members 15 and 16, and the resilient and elastic members 15 and 16 are sandwiched and fixed between the sheet joined sections 70.

When the sheet joined sections 70 are formed by welding, the welded portions 75 become inevitably hardened. However, the influence of the hardening is limited when the dimensions of the sheet joined sections 70 fall within the foregoing range. In addition, the welding process produces a secondary effect that the welded portions 75 are higher in transparency and appear to be glossy in a striped pattern.

Spacings $15d$ and $16d$ between the adjacent resilient and elastic members 15 and 16 can be decided as appropriate. However, when the spacings $15d$ and $16d$ exceed 10 mm, the thickness of the ridges 80 changes in the direction intersecting with the extending direction and the ridges 80 take the shape of fluffy feel clouds or waves, although it is not more prominent than in the vertical intermittent joining mode. Accordingly, in the present invention, the spacings $15d$ and $16d$ between the adjacent resilient and elastic members 15 and 16 are preferably 10 mm or less, more specifically 3 to 7 mm.

The fineness and extension ratio (in the fully opened elastic structure) of the resilient and elastic members 15 and 16 can be selected as appropriate according to the attachment positions of the resilient and elastic members 15 and 16. The preferred ranges of the fineness and extension ratio are as described above. As a whole, the resilient and elastic members 15 and 16 desirably have a fineness of about 300 to 1,000 dtex, and an extension ratio of about 200 to 350%.

In the elastic structure described above, as illustrated in FIG. 6(b), with the contraction of the resilient and elastic members 15 and 16, the portions of the first sheet material 12S and the second sheet material 12H positioned between the sheet joined sections 70 are also contracted and swelled in mutually opposite directions to form the ridges 80. FIG. 6(b) illustrates the resilient and elastic members 15 and 16 in the natural strength state. When the diaper is worn, the resilient and elastic members 15 and 16 are elongated to some degree such that the ridges 80 spread toward the bottom and height $80h$ of the ridges 80 becomes decreased as illustrated in FIG. 6(c). In addition, the elastic structure is formed in the vertical continuous joining mode, and the ridges 80 are extended in a straight line along the sheet joined sections 70 with excellent air permeability and appearance.

The width $70w$ of the sheet joined sections 70 in the extending direction affects the spacing between the adjacent ridges 80. When the ridges 80 are thin as in the vertical continuous joining mode and the width $70w$ of the sheet joined sections 70 is larger than 4 mm, the spacing between the adjacent ridges 80 is excessively large to make the individual ridges 80 appear to be independent from each other. In addition, when the ridges 80 are deformed to be flattened and spread or fallen by the contraction force in the thickness direction, the adjacent ridges 80 support imperfectly each other and become weakened in resistance against deformation and recovery from deformation, thereby resulting in insufficient fluffy feel.

Further, when the width $70w$ of the sheet joined sections 70 in the extending direction is 0.5 to 4 mm but the spacing $70d$ between the adjacent sheet joined sections 70 is less than 4 mm or larger than 8 mm, some problems will arise as described below. The spacing $70d$ between the adjacent joined sections 70 affects the height $80h$ and width of the ridges 80. With a spacing of about 2 mm, the ridges 80 are insufficient in vertical continuity as in the case where the sheet materials are fixed continuously in the extending direction (it is useless to provide the intermittent sheet joined sections 70 in the extending direction). Meanwhile, with a spacing of 3 mm, the ridges 80 are extended in a straight line in the direction orthogonal to the extending direction, but the adjacent ridges 80 support insufficiently each other with a shortage of fluffy feel. When the spacing $70d$ between the sheet joined sections 70 is more than 8 mm, the ridges 80 are randomly compressed and crushed at the time of packaging, which deteriorates the appearance of the product. In contrast, when the width $70w$ of the sheet joined sections 70 in the extending direction is set to 0.5 to 4 mm and the spacing $70d$ between the sheet joined sections 70 is set to 4 to 8 mm, the ridges 80 produce sufficient fluffy feel and become less prone to be randomly compressed and crushed at the time of packaging. In the vertical continuous joining mode, when the sheet joined sections 70 are formed by welding, hard streaks are generated with inevitable reduction in flexibility. In the present invention, however, the sheet joined sections 70 are formed by the adhesive 71 without reduction in flexibility resulting from material welding, thereby providing further excellent flexibility.

The first sheet material 12S and the second sheet material 12H are preferably non-woven fabric. However, if the bending resistance is low in the extending direction, the ridges 80 become thin and sharp in shape, likely to be fallen, and poor in compression resilience in the thick direction. To solve these problems, the basis weight of the non-woven fabric may be increased. In this case, however, the sheet materials may become stiff (due to excessively high rigidness) and less soft to the touch in spite of their fluffy appearances. Meanwhile, when the first sheet material 12S and the second sheet material 12H are made from non-woven fabric in which the bending resistance is higher in the extending direction than in the direction orthogonal to the extending direction, the ridges 80 are likely to be roundly swelled, increased in compression resilience in the thickness direction, less prone to be fallen, and improved in softness to the touch. The bending resistance of the first sheet material 12S and the second sheet material 12H in the extending direction is preferably 30 to 75 mm, more specifically 40 to 55 mm. The bending resistance of the first sheet material 12S and the second sheet material 12H in the direction orthogonal to the extending direction is preferably 20 to 50 mm, more specifically 25 to 35 mm, within the range lower than the bending resistance in the extending direction.

The bending resistance of non-woven fabric is measured according to JIS L1096: 2010 "Testing methods for woven and knitted fabrics," bending resistance A method (45-degree cantilever method).

To set the bending resistance of non-woven fabric in the direction orthogonal to the extending direction to be lower than the bending resistance in the extending direction, the orientation of fibers in the non-woven fabric is set along the extending direction. The orientation of fibers is the direction along which the fibers in non-woven fabric are aligned. "Setting the orientation of fibers along the extending direction" covers the mode in which a total weight of fibers constituting the non-woven fabric is oriented along the extending direction and the mode in which a more than 50% weight of fibers is oriented within the range of $-45°$ to $+45°$ relative to the extending direction. The orientation of fibers in the non-woven fabric can be measured by any of commonly used measurement methods. For example, the measurement method may be a measurement method according to TAPPI STD T481, fiber orientation testing by zero-span tensile strength, or may be a simple measurement method by which the fiber orientation is decided from the ratio of tensile strengths in the extending direction and the direction orthogonal to the extending direction. According to the latter simple measurement method, a specimen 200 mm long and 50 mm wide is under tensile testing by a tensile strength tester on the conditions that the crosshead speed is 500 mm/min and the inter-chuck distance is 150 mm, thereby to determine the tensile strength from the maximum load under tension. When the tensile strength ratio (extending direction/direction orthogonal to the extending direction) is larger than 1, it is determined that the fibers are oriented along the extending direction.

In the elastic structure of the present invention, the sheet joined sections 70 are intermittently provided in the extending direction, and the fixing force of the resilient and elastic members 15 and 16 inevitably becomes lowered, and the resilient and elastic members 15 and 16 may come off. In particular, the width 70w of the sheet joined sections 70 is desirably narrow in the extending direction, but in this case, the resilient and elastic members 15 and 16 and the sheet joined sections 70 intersect each other at smaller points. That is, the resilient and elastic members 15 and 16 need to be fixed at the smaller points. Accordingly, it is important to assure the fixing force of the resilient and elastic members 15 and 16.

Figure 9:
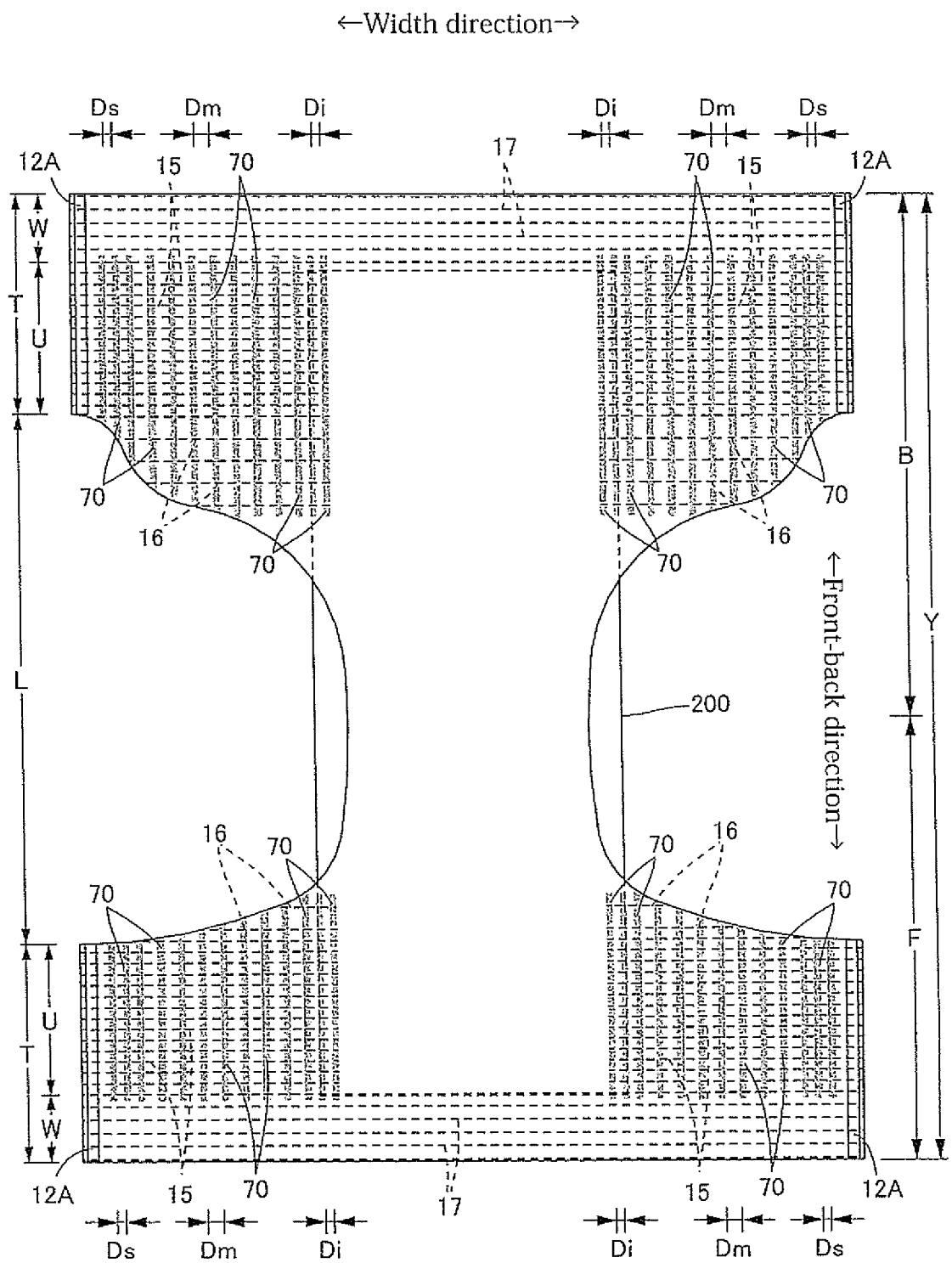
FIG. 9 is a planar view of an outer surface of an underpants-type disposable diaper in an open state.

To solve this issue, as illustrated in FIG. 9, the areas of the outer body 12 at the both sides along the width direction of the inner body 200 are divided into end areas at the inner body 200 side, end areas at the side seal portion 12A side, and intermediate areas between the former areas, and spacings Di and Ds between the sheet joined sections 70 in the end areas at the inner body 200 side and the end areas at the side seal portion 12A side is desirably narrower than spacing Dm between the sheet joined sections 70 in the intermediate areas.

Figure 10:
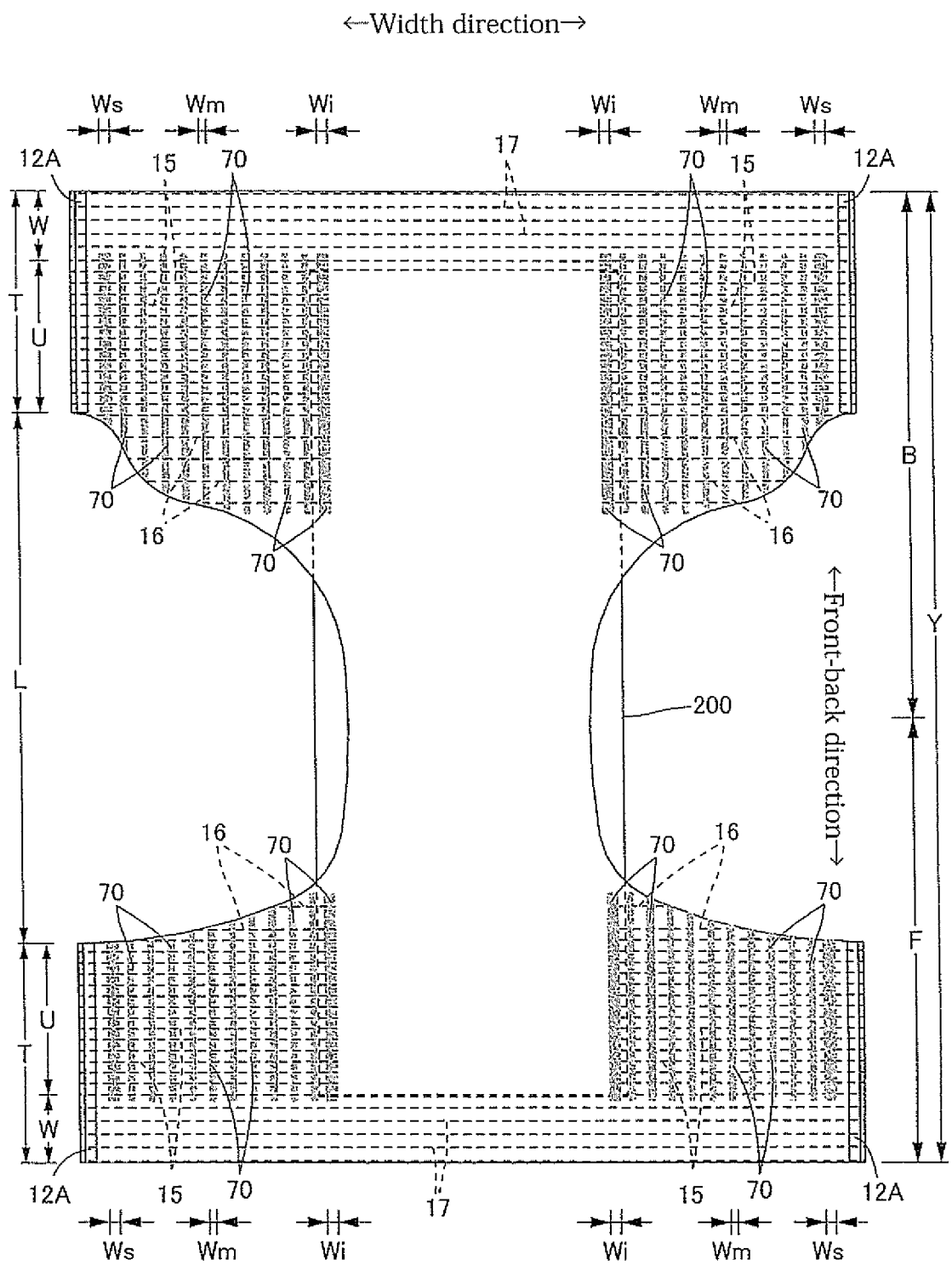
FIG. 10 is a planar view of an outer surface of an underpants-type disposable diaper in an open state.

Instead of the mode illustrated in FIG. 9 (or in combination with the mode illustrated in FIG. 9), as illustrated in FIG. 10, fixed widths Wi and Ws of the resilient and elastic members 15 and 16 in the end areas of the inner body 200 side and the end areas of the side seal portions 12A side (in the illustrated mode, the fixed widths Wi and Ws are equal to the width 70w of the sheet joined sections 70 in the extending direction) may be preferably larger than fixed width Wm of the resilient and elastic members in the intermediate areas.

The resilient and elastic members 15 and 16 of the underpants-type disposable diaper 12 are firmly fixed by the side seal portions 12A at the ends of the outside in the width direction. Accordingly, the foregoing fixation reinforcement means may be omitted in the end areas at the side seal portion 12A sides.

(Others)

In the foregoing examples, the elastic structure is applied to the range from the waist lower portions U to the intermediate portion L of the underpants-type disposable diaper. Besides, the elastic structure may also be applied to the waist edge portions W. The resilient and elastic members 16 may be omitted from the intermediate portion L. In addition, the foregoing elastic structure can also be applied to the waist portion of the back side of the tape-type disposable diaper described above in relation to the related art, the three-dimensional gathers, and other elastic portions.

<Experiment 1>

Polypropylene-fiber SSS non-woven fabric with a fineness of 1.6 denier, a basis weight of 17 g/m$^2$, a thickness of 0.2 mm (initial thickness TO under a pressure of 0.5 g/cm$^2$), a bending resistance of 55 mm in the MD direction (along the manufacturing line of the non-woven fabric), and a bending resistance of 28 mm in the CD direction (orthogonal to the MD direction) was cut into a first sheet material and a second sheet material with a length of 180 mm in the MD direction and a length of 40 mm in the CD direction. In addition, 470-dtex rubber threads were prepared as resilient and elastic members.

A hot-melt adhesive was applied with a width of 1 mm to the surface of the first sheet material at the second sheet material side continuously in the CD direction with spacing of 7 mm in the MD direction. Then, seven rubber threads were arranged on the surface of the first sheet material continuously in the MD direction in an elongated state at an extension ratio of 270% with intervals of 5 mm in the CD direction. The second sheet material was laid on the rubber threads to be aligned with the first sheet material in the MD direction and CD direction. The first sheet material, the resilient and elastic members, and the second sheet material were pressed and attached to one another to fabricate an elastic sheet sample No. 1. The natural length of the sample No. 1 was 67 mm in the MD direction. Further, samples No. 2 to 13 were fabricated with changes as appropriate in application width of the hot-melt adhesive to 2 mm, 4 mm, 6 mm, and 10 mm and with changes as appropriate in application intervals of the hot-melt adhesive to 2 mm, 4 mm, 6 mm, 8 mm, and 10 mm.

The formation status of ridges in these samples were observed and evaluated on a four-scale basis: ⊚: the ridges were formed in a very excellent manner; ○: the ridges were formed in an excellent manner; Δ: the ridges were formed in a non-excellent manner; and x: the ridges were formed in an insufficient manner. Table 1 shows the evaluation results. With application intervals of the hot-melt adhesive of 10 mm, the ridges were formed but crushed due to their large size at the time of compression. With application intervals of the hot-melt adhesive of 2 mm, the ridges were not formed. With application intervals of the hot-melt adhesive of 6 mm and 10 mm, the sheet joined sections were also contracted to form wrinkles.

TABLE 1

|  | No. 1 Example 1 | No. 2 Example 2 | No. 3 Example 3 | No. 4 Example 4 | No. 5 Example 5 | No. 6 Example 6 | No. 7 Comparative Example 1 | No. 8 Comparative Example 2 | No. 9 Comparative Example 3 | No. 10 Comparative Example 4 | No. 11 Comparative Example 5 | No. 12 Comparative Example 6 | No. 13 Comparative Example 7 |
|---|---|---|---|---|---|---|---|---|---|---|---|---|---|
| Hot-melt adhesive application width (mm) | 1 | 2 | 2 | 2 | 4 | 4 | 2 | 2 | 6 | 6 | 6 | 10 | 10 |
| Hot-melt adhesive application intervals (mm) | 7 | 4 | 6 | 8 | 4 | 6 | 2 | 10 | 2 | 4 | 6 | 6 | 10 |

TABLE 1-continued

|  | No. 1 Example 1 | No. 2 Example 2 | No. 3 Example 3 | No. 4 Example 4 | No. 5 Example 5 | No. 6 Example 6 | No. 7 Comparative Example 1 | No. 8 Comparative Example 2 | No. 9 Comparative Example 3 | No. 10 Comparative Example 4 | No. 11 Comparative Example 5 | No. 12 Comparative Example 6 | No. 13 Comparative Example 7 |
|---|---|---|---|---|---|---|---|---|---|---|---|---|---|
| Observation results of ridges formation status | ⊚ | ○ | ⊚ | ⊚ | ○ | ⊚ | X | Δ | X | X | Δ | Δ | Δ |

⊚: The ridges were formed in a very excellent manner
○: The ridges were formed in an excellent manner
Δ: The ridges were formed in a non-excellent manner
X: The ridges were formed in an insufficient manner The experiment 1 has revealed that the desired results could be obtained when the hot-melt adhesive application width (that is, the width of the sheet joined sections in the extending direction) was 0.5 to 4 mm and the hot-melt adhesive application intervals (that is, the spacing between the adjacent sheet joined sections) were 4 to 8 mm.

<Experiment 2>

An elastic sheet sample No. 14 was fabricated in the same manner as in the experiment 1 (however, the hot-melt adhesive application width was 2 mm and the hot-melt adhesive application intervals were 6 mm).

A sample No. 15 was fabricated in the same manner as the sample No. 14 except that the hot-melt adhesive was applied continuously in the MD direction of the first sheet material and the second sheet material, and the rubber threads were arranged continuously in the CD direction of the first sheet material and the second sheet material.

Five each ridges in the samples No. 14 and No. 15 in the natural length state were measured for compression characteristics (compression stiffness LC, compression energy WC, compression resilience RC, initial thickness T0, and maximum-load thickness TM) by setting the center of a pressure plate described later to the peaks of the ridges, and the measured values were averaged. For the compression stiffness LC, a value closer to 1 is higher in stiffness. For the compression energy WC, a larger value is more prone to be compressed. For the compression resilience RC, a value closer to 100 is higher in compression recovery performance. The initial thickness T0, the compression stiffness LC, the compression energy WC, and the compression resilience RC are measured by the use of a KES-FB3-AUTO-A automated compression tester under KES (Kawabata's Evaluation System for Fabrics). A specimen was compressed between disc-shaped planes of steel press plates with a compression area of 2 cm² at compression loads of 0 to 50 gf/cm², and was measured until the specimen was returned to its original state. The initial thickness T0 refers to the thickness of the specimen under a pressure of 0.5 gf/cm². The compression stiffness LC indicates the linearity of compression displacement, and its value is larger with a higher proportionality between load and displacement (reduction in thickness due to compression). The compression energy WC indicates the work of compression, and its higher value results in more excellent fluffy feel and stiffness. The compression resilience RC indicates compression recovery performance, and its higher value results in smaller hysteresis.

TABLE 2

|  |  | Sample No. 14 Example 7 | Sample No. 15 Example 8 |
|---|---|---|---|
| LC | (—) | 1.15 | 0.91 |
| WC | (gfcm/cm²) | 1.63 | 2.00 |
| RC | (%) | 53.3 | 42.7 |
| T0 | (mm) | 6.44 | 6.18 |
| TM | (mm) | 3.60 | 1.78 |
| T0 − TM | (mm) | 2.83 | 4.40 |
| INT | (—) | 16.3 | 20.0 |
| B-INT | (—) | 8.68 | 8.54 |
| GAP | (mm) | 7.02 | 6.62 |

Figure 16:
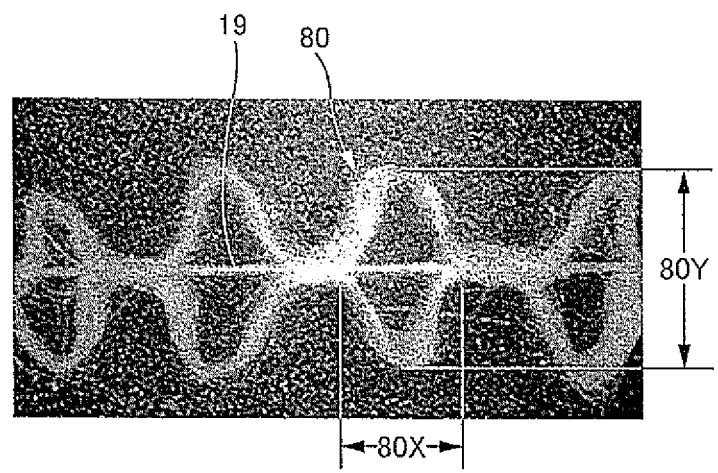
FIG. 16 shows microscope photographs.
Figure 16:
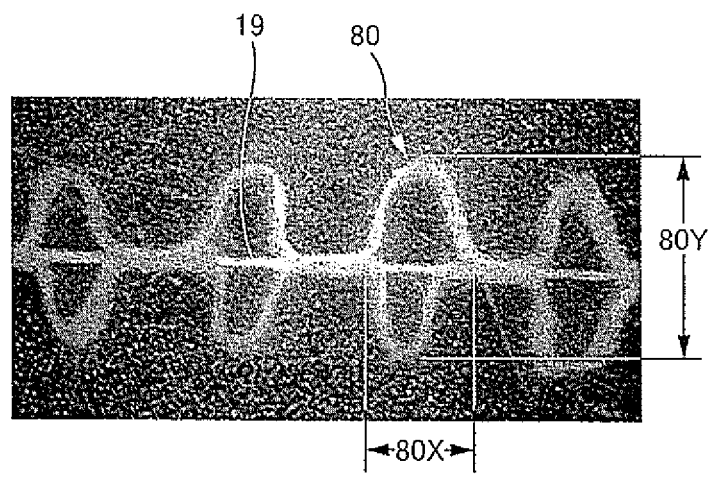

In addition, the samples No. 14 and No. 15 were elongated about 1.65 times in the MD direction (the assumed diaper wearing state), and were micrographed (at a 30-fold magnification) from the side. From the micrographs, apparent heights 80Y and widths 80X of the ridges 80 in the samples were measured and averaged. FIG. 16 shows the micrographs, and Table 3 shows the heights and widths of the ridges. The micrography was performed by the use of a digital microscope VHX-1000 produced by Keyence Corporation.

TABLE 3

|  |  | Sample No. 14 Comparative Example 7 | Sample No. 15 Comparative Example 8 |
|---|---|---|---|
| Height | (µm) | 4637 | 4467 |
| Width | (µm) | 3734 | 3008 |

The experiment 2 has revealed that, when the bending resistance of the non-woven fabric was higher in the extending direction than in the direction orthogonal to the extending direction, the ridges were likely to be roundly swelled, higher in compression recovery performance in the thickness direction, less prone to be fallen, and excellent in softness to the touch.

<Experiment 3>

The same first sheet material, resilient and elastic members, and second sheet materials as those in the experiment 1, and various kinds of hot-melt adhesives different in melt viscosity and loop tack adhesive force were prepared. Adhesion test was performed on the prepared specimens at a line speed of 187 m/minute on the same equipment as illustrated in FIG. 15 to check the stability of operation in relation to the stringiness of the hot-melt adhesives and the like. The stability of operation was evaluated on a two-scale basis: o: the adhesion was stably conducted without stringiness; and x: the operation stability is insufficient at a low application width accuracy due to stringiness.

TABLE 4

| | | Hot-melt adhesive types | | | | |
|---|---|---|---|---|---|---|
| | | A | B | C | D | E |
| Melt viscosity | 140 °C. | 4030 | 6030 | 6900 | 17500 | 21500 |
| (mpas) | 160 °C. | 1750 | 2950 | 3000 | 7080 | 8100 |
| Loop tack | (g/25 mm) | 2710 | 2550 | 1560 | 980 | 40 |
| Evaluation | | ○ | ○ | X | X | X |

The experiment 3 has revealed that desired results were obtained when the hot-melt adhesive had a melt viscosity of 10000 mpas or less at a temperature of 140° C., a melt viscosity of 5000 mpas or less at a temperature of 160° C., and a loop tack adhesive force of 2000 g/25 mm or more.

Descriptions of the Terms Used Herein

Unless otherwise specified herein, the terms used herein have the meanings described below.
(Gel strength)
The gel strength is measured in such a manner as described below. That is, a high-absorbent polymer of 1.0 g is added to an artificial urine of 49.0 g (urea: 20 wt %, salt: 8 wt %, calcium chloride dehydrate: 0.3 wt %, magnesium oxide heptahydrate: 0.8 wt %, and pure water: 70.01 wt %), and then the mixture is agitated with a stirrer. The resultant gel is left stand for three hours in a constant temperature and humidity chamber at 40° C. and 60% RH, and then returned to a room-temperature environment. Then, the gel strength is measured by a curd meter (Curdmeter-MAX ME-500 produced by I. Techno Engineering Co., Ltd.)
(Basis weight)
The basis weight is measured in such a manner as described below. That is, a specimen or a test piece is preliminarily dried and left stand in a test room or a test device in a standard state (at a temperature of 20±5° C. and a relative humidity of 65% or less) until reaching a constant weight. The preliminary drying refers to turning the specimen or the test piece to a constant weight in an environment at a relative humidity of 10 to 25% and a temperature not exceeding 50° C. The preliminary drying is not necessary for fibers with an official moisture regain of 0.0%. The test piece of the constant weight is cut into a 200 mm×250 mm (±2 mm) specimen by the use of a basis weight plate (200 mm×250 mm±2 mm). The weight of the specimen is measured and the measured value is multiplied by 20 to determine the weight per square meter as a basis weight.
(Thickness)
The thickness is automatically measured by an automated thickness gauge (KES-G5 handy compression measurement program) on the conditions that the load is 10 gf/cm$^2$ and the pressure area is 2 cm$^2$).

INDUSTRIAL APPLICABILITY

The present invention is suited to underpants-type disposable diapers as described above but is also applicable to tape-type or pad-type disposable diapers and other general absorbent articles such as sanitary napkins.

REFERENCE SIGNS LIST

11 Liquid impervious sheet
12 Outer body
12A Side seal portion
12H Second sheet material
12S First sheet material
12r Folded portion
200 Inner body
30 Face sheet
40 Intermediate sheet
50 Absorbent element
56 Absorber
58 Wrapping sheet
60 Three-dimensional gather
62 Gather sheet
70 Sheet joined section
71 Adhesive
80 Ridge

The invention claimed is:
1. An elastic structure for absorbent article, comprising:
a first sheet material;
a second sheet material opposed to one surface of the first sheet material; and
a plurality of elongated resilient and elastic members that is provided between the first sheet material and the second sheet material along an extending direction with spacing therebetween, wherein:
the first sheet material and the second sheet material are joined together to form sheet joined sections by an adhesive applied intermittently in the extending direction and continuously in a direction intersecting with the extending direction,
the second sheet material has a surface configured to contact a wearer's skin,
the first sheet material is joined to a surface of the second sheet material opposite to the surface configured to contact the wearer's skin,
the resilient and elastic members are fixed by the adhesive to the first sheet material or the second sheet material at intersections with the sheet joined sections,
at the intersections between the sheet joined sections and the resilient and elastic members, the adhesive is continuous on the first sheet material side in the direction intersecting with the extending direction, so that the resilient and elastic members are fixed by the adhesive to the first sheet material, and the adhesive is discontinuous the second sheet material side in the direction intersecting with the extending direction,
when the first sheet material and the second sheet material are contracted with contraction of the resilient and elastic members, portions of the first sheet material and the second sheet material positioned between the sheet joined sections are swelled in mutually opposite directions to form ridges,
the sheet joined sections have a width of 0.5 to 2 mm in the extending direction and spacing between the adjacent sheet joined sections is 5 mm to 7 mm;
the first sheet material is a non-woven fabric in which the thickness is 0.1 to 1 mm, the basis weight is 10 g/m$^2$ to 20 g/m$^2$, the bending resistance in the extending direction is 40 mm to 55 mm and the bending resistance in the direction orthogonal to the extending direction is 25 mm to 35 mm and the second sheet material is a non-woven fabric in which the thickness is 0.1 to 1 mm, the basis weight is 10 g/m$^2$ to 20 g/m$^2$, the bending resistance in the extending direction is 40 mm to 55 mm and the bending resistance in the direction orthogonal to the extending direction is 25 mm to 35 mm, and an extension ratio of the resilient and elastic members is 200% to 350% in a state where the elastic structure is fully opened.

2. The elastic structure for absorbent article according to claim 1, wherein the adhesive is a hot-melt adhesive with a melt viscosity of 10000 mPa·S or less at a temperature of 140° C., a melt viscosity of 5000 mPa·S or less at a temperature of 160° C., and a loop tack adhesive force of 2000 g/25 mm or more.

3. The elastic structure for absorbent article according to claim 1, wherein the spacing between the adjacent resilient and elastic members is 10 mm or less.

* * * * *